(12) United States Patent
Guan et al.

(10) Patent No.: US 8,889,791 B2
(45) Date of Patent: Nov. 18, 2014

(54) THERMORESPONSIVE, BIODEGRADABLE, ELASTOMERIC MATERIAL

(75) Inventors: Jianjun Guan, Pittsburgh, PA (US); William R. Wagner, Wexford, PA (US); Kazuro Lee Fujimoto, Pittsburgh, PA (US)

(73) Assignee: University of Pittsburgh-Of the Commonwealth System of Higher Education, Pittsburgh, PA (US)

( * ) Notice: Subject to any disclaimer, the term of this patent is extended or adjusted under 35 U.S.C. 154(b) by 1446 days.

(21) Appl. No.: 11/869,774

(22) Filed: Oct. 10, 2007

(65) Prior Publication Data
US 2008/0096975 A1    Apr. 24, 2008

Related U.S. Application Data

(60) Provisional application No. 60/850,642, filed on Oct. 10, 2006.

(51) Int. Cl.
| | | |
|---|---|---|
| *A61K 47/34* | (2006.01) | |
| *A61K 47/38* | (2006.01) | |
| *C08G 63/46* | (2006.01) | |
| *C12N 5/02* | (2006.01) | |
| *C08F 265/10* | (2006.01) | |
| *C08F 290/06* | (2006.01) | |
| *A61L 27/16* | (2006.01) | |
| *A61K 47/48* | (2006.01) | |
| *A61L 27/38* | (2006.01) | |
| *C08F 265/00* | (2006.01) | |
| *C08F 265/04* | (2006.01) | |
| *C08L 51/00* | (2006.01) | |
| *A61K 9/00* | (2006.01) | |

(52) U.S. Cl.
CPC .............. *A61K 47/482* (2013.01); *C08F 265/10* (2013.01); *C08F 290/06* (2013.01); *A61L 27/16* (2013.01); *A61K 47/34* (2013.01); *A61K 47/48176* (2013.01); *A61L 27/3873* (2013.01); *C08F 265/00* (2013.01); *C08F 265/04* (2013.01); *C08L 51/003* (2013.01); *A61K 47/48784* (2013.01); *A61K 9/0019* (2013.01)
USPC .......... 525/190; 525/54.1; 536/22.1; 514/1.1; 514/772.4; 514/42; 514/43; 424/93.1; 424/93.6; 424/422; 424/426; 424/486

(58) Field of Classification Search
CPC ...... C08L 51/003; A61K 38/02; A61K 47/32; A61K 47/34; A61K 47/48; A61K 47/48176
USPC ................... 536/22.1; 514/1.1, 772.4, 42, 43; 525/54.1, 190; 424/93.1, 93.6, 422, 424/426, 486
See application file for complete search history.

(56) References Cited

U.S. PATENT DOCUMENTS

| | | | |
|---|---|---|---|
| 5,053,228 A | 10/1991 | Mori et al. | |
| 5,124,421 A | 6/1992 | Ulbrich et al. | |
| 5,610,241 A | 3/1997 | Lee et al. | |
| 5,702,717 A | 12/1997 | Cha et al. | |
| 5,807,581 A * | 9/1998 | Rosenblatt et al. | 424/484 |
| 6,030,634 A | 2/2000 | Wu et al. | |
| 6,458,889 B1 | 10/2002 | Trollsas et al. | |
| 6,833,408 B2 | 12/2004 | Sehl et al. | |
| 6,841,617 B2 | 1/2005 | Jeong et al. | |
| 6,979,464 B2 * | 12/2005 | Gutowska | 424/484 |
| 7,094,418 B2 | 8/2006 | Chudzik et al. | |
| 2002/0015734 A1 * | 2/2002 | Uludag et al. | 424/486 |
| 2004/0001892 A1 | 1/2004 | Healy et al. | |
| 2005/0238722 A1 | 10/2005 | Pathak et al. | |
| 2005/0260179 A1 | 11/2005 | Fishman et al. | |
| 2006/0034889 A1 * | 2/2006 | Jo et al. | 424/426 |

FOREIGN PATENT DOCUMENTS

WO    WO 2004/014969 A1 *   2/2004

OTHER PUBLICATIONS

Lee et al. (Macromolecular Bioscience, vol. 5, Issue 7, p. 629-635, Published online Jul. 14, 2005).*
Li et al. (Proceedings of the National Academy of Sciences, vol. 100, No. 26, p. 15346-15351, Published Dec. 23, 2003).*
Ibusuki et al. (Tissue Engineering, vol. 9, No. 2, p. 371-384 , Published 2003).*
Guan et al. (Biomacromolecules, 2008, 9, 1283-1292).*
Tous et al. (Biomacromolecules, 2011, 12, 4127-4135).*
Au A, Ha J, Polotsky A, Krzyminski K, Gutowska A, Hungerford DS, Frondoza CG. Thermally reversible polymer gel for chondrocyte culture. J Biomed Mater Res A. Dec. 15, 2003;67(4):1310-9.
Bromberg LE, Ron ES. Temperature-responsive gels and thermogelling polymer matrices for protein and peptide delivery. Adv Drug Deliv Rev. May 4, 1998;31(3):197-221.
Cao YL, et al. Preparation and use of thermosensitive polymers. In: Morgan JR, Yarmush ML, eds. Methods in Molec Med: Tissue engineering Methods and Protocols. Totowa, N.J., Humana Press, 1999, pp. 75-84.
Cho JH, et al. Chondrogenic differentiation of human mesenchymal stem cells using a thermosensitive poly(N-isopropylacrylamide) and water-soluble chitosan copolymer. Biomaterials. Nov. 2004;25(26):5743-51.
Drury JL, Mooney DJ. Hydrogels for tissue engineering: scaffold design variables and applications. Biomaterials. Nov. 2003;24(24):4337-51.
Elbjeirami WM, Yonter EO, Starcher BC, West JL. Enhancing mechanical properties of tissue-engineered constructs via lysyl oxidase crosslinking activity. J Biomed Mater Res A. Sep. 1, 2003;66(3):513-21.

(Continued)

*Primary Examiner* — Johann R Richter
*Assistant Examiner* — Alma Pipic
(74) *Attorney, Agent, or Firm* — The Webb Law Firm

(57) ABSTRACT

Provided are novel biocompatible copolymers and compositions comprising the copolymers. The copolymers and degradation products thereof are non-toxic and typically have an LCST between room temperature and 37° C. so that they are liquid at room temperature and gelled at 37° C. which facilitates their use in humans, for example for wound treatment and as a cellular growth matrix or niche. The copolymer comprises numerous ester linkages in its backbone so that the copolymers are erodeable in situ. Degradation products of the polymer are soluble and non-toxic. The copolymer is amine-reactive so that it can conjugate with proteins, such as collagen. Active ingredients, such as drugs, can be incorporated into compositions comprising the copolymer.

28 Claims, 37 Drawing Sheets

(56) References Cited

OTHER PUBLICATIONS

Feil H, Bae TH, Feijen J, Kim SW. Effect of comonomer hydrophilicity and ionization on the lower critical solution temperature of N-isopropylacrylamide copolymers. Macromolecules. 1993;26(10);2496-2500.

Guan J, Wagner WR. Synthesis, characterization and cytocompatibility of polyurethaneurea elastomers with designed elastase sensitivity. Biomacromolecules. Sep.-Oct. 2005;6(5):2833-42.

Gutowska A, Jeong B, Jasionowski M. Injectable gels for tissue engineering. Anat Rec. Aug. 1, 2001;263(4):342-9.

Han CK, Bae YH. Inverse thermally-reversible gelation of aqueous N-isopropylacrylamide copolymer solutions. Polymer. Jun. 1998;39(13):2809-14.

Healy KE, Rezania A, Stile RA. Designing biomaterials to direct biological responses. Ann N Y Acad Sci. Jun. 18, 1999;875:24-35.

Hennink WE, van Nostrum CF. Novel crosslinking methods to design hydrogels. Adv Drug Deliv Rev. Jan. 17, 2002;54(1):13-36.

Hoerstrup SP, Zünd G, Sodian R, Schnell AM, Grünenfelder J, Turina MI. Tissue engineering of small caliber vascular grafts. Eur J Cardiothorac Surg. Jul. 2001;20(1):164-9.

Kim S, et al. Synthetic MMP-13 degradable ECMs based on poly(N-isopropylacrylamide-co-acrylic acid) semi-interpenetrating polymer networks et al. J Biomed Mater Res A. Oct. 1, 2005;75(1):73-88.

Kim S, Healy KE. Synthesis and characterization of injectable poly(N-isopropylacrylamide-co-acrylic acid) hydrogels with proteolytically degradable cross-links. Biomacromolecules. Sep.-Oct. 2003;4(5):1214-23.

Lee BH, Vernon B. Copolymers of N-isopropylacrylamide, HEMA-lactate and acrylic acid with time-dependent lower critical solution temperature as a bioresorbable . . . Polymer Int. Feb. 2005;54(2):418-22.

Lee BH, Vernon B. In situ-gelling, erodible N-isopropylacrylamide copolymers. Macromol Biosci. Jul. 14, 2005;5(7):629-35.

Li F, et al. Cellular and nerve regeneration within a biosynthetic extracellular matrix for corneal transplantation. Proc Natl Acad Sci U S A. Dec. 23, 2003;100(26):15346-51. Epub Dec. 5, 2003.

Li F, et al. Recruitment of multiple cell lines by collagen-synthetic copolymer matrices in corneal regeneration. Biomaterials. Jun. 2005;26(16):3093-104.

Makino K, Hiyoshia J, Ohshima H. Kinetics of swelling and shrinking of poly (N-isopropylacrylamide) hydrogels at different temperatures. Colloids Surf B: Biointerfaces. Dec. 15, 2000;19(2):197-204.

Matsumaru Y, Hyodo A, Nose T, Ito S, Hirano T, Ohashi S. Application of thermosensitive polymers as a new embolic material for intravascular neurosurgery. J Biomater Sci Polym Ed. 1996;7(9):795-804.

Nancollas H. In vitro studies of calcium phosphate crystallization. In: Mann S, Webb J, Williams RPJ, eds. Biomineralization: Chemical and biochemical perspectives. New York: VCH, 1989, pp. 157-187.

Neradovic D, et al. Poly(N-isopropylacrylamide) with hydrolyzable lactic acid ester side groups: a new type of thermosensitive polymer. Macromolecular Rapid Comm. Oct. 1999;20(I1): 577-81.

Ohya S, Matsuda T. Poly(N-isopropylacrylamide) (PNIPAM)-grafted gelatin as thermoresponsive-three-dimensional artificial extracellular matrix: molecular . . . J Biomater Sci Polym Ed. 2005;16(7):809-27.

Ohya S, et al. Thermoresponsive artificial extracellular matrix for tissue engineering:hyaluronic acid bioconjugated with poly(N-isopropylacrylamide) grafts. Biomacromolecules. 2001 Fall;2(3):856-63.

Opitz F, et al. Tissue engineering of ovine aortic blood vessel substitutes using applied shearstress and enzymatically derived vascular smooth muscle cells. Ann Biomed Eng. Feb. 2004;32(2):212-22.

Ray JL, Leach R, Herbert JM, Benson M. Isolation of vascular smooth muscle cells from a single murine aorta. Methods Cell Sci. 2001;23(4):185-8.

Schmedlen RH, Masters KS, West JL. Photocrosslinkable polyvinyl alcohol hydrogels that can be modified with cell adhesion peptides for use in tissue engineering. Biomaterials. Nov. 2002;23(22):4325-32.

Schmolka IR. Artificial skin. I. Preparation and properties of pluronic F-127 gels for treatment of burns. J Biomed Mater Res. Nov. 1972;6(6):571-82.

Shimizu T, et al. Fabrication of pulsatile cardiac tissue grafts using a novel 3-dimensional cellsheet manipulation technique and temperature-responsive cell culture . . . Circ Res. Feb. 22, 2002;90(3):e40-48.

Stile RA, Healy KE. Thermo-responsive peptide-modified hydrogels for tissue regeneration Biomacromolecules. 2001 Spring;2(1):185-94.

Tiwari A, Salacinski HJ, Punshon G, Hamilton G, Seifalian AM. Development of a hybrid cardiovascular graft using a tissue engineering approach. Faseb J. Jun. 2002;16(8):791-6.

van Dijk-Wolthuis WNE, et al. A new class of polymerizable dextrans with hydrolyzable groups: hydroxyethyl methacrylated dextran with and without oligolactate . . . Polymer. Dec. 1997;38(25):6235-42.

Vihola H, et al. Cytotoxicity of then-nosensitive polymers poly(N-isopropylacrylamide),poly(N-vinylcaprolactam) and amphiphilically modified . . . Biomaterials. Jun. 2005;26(16):3055-64.

* cited by examiner

PNIPAAm-  PNIPAAm-NHS-

THERMORESPONSIVE, BIODEGRADABLE, ELASTOMERIC MATERIAL

CROSS REFERENCE TO RELATED APPLICATIONS

This application claims the benefit under 35 U.S.C. §119(e) of U.S. Provisional Application No. 60/850,642, filed on Oct. 10, 2006, which is incorporated herein by reference in its entirety.

STATEMENT REGARDING FEDERAL FUNDING

The U.S. Government has a paid-up license in this invention and the right in limited circumstances to require the patent owner to license others on reasonable terms as provided for by the terms of Grant No. R01 HL 069368 awarded by the National Institutes of Health.

A thermoresponsive, biodegradable elastomeric material is described herein, along with methods of making the material and uses for the material.

Two- and three-dimensional polymer/hydrogel matrices provide a diverse scaffold that can be modified and refined for various purposes. Hydrogels can be applied to various medical, engineering, biological and chemical applications, such as drug or chemical delivery, tissue engineering, cell transplantation, wound healing and rheology modification. To realize these purposes, current technologies aim to control the physical and biological properties of the hydrogel matrix, including, without limitation: strength; hydrophobicity/hydrophilicity; elasticity; biodegradation rate; reactivity with other compounds or compositions, such as specific or non-specific binding to proteins or peptides; toxicity; shrinking and expanding rate and pore size. As variations in the composition or in preparation of the hydrogel can result in different physical properties, the types of hydrogel matrices available are many, though not exhaustive. By combining and controlling different physical properties within the hydrogel matrix, new properties of the hydrogel may be discovered, and the usefulness of the hydrogel for particular purposes can be increased.

Wu et al. (U.S. Pat. No. 6,030,634) disclose a polymer gel composite composed of a pure polymer matrix of N-isopropylacrylamide and an interpenetrating matrix of N-isopropylacrylamide with a hydrophilic protein, such as gelatin or collagen. This composite gel was molded into various shapes or disks and then implanted around blood vessels and neurons to aid in repair of damaged tissues.

Trollsas et al. (U.S. Pat. No. 6,458,889) disclose a hydrogel composed of a cross-linkable polynucleophilic component, a cross-linkable polyelectrophilic component and a cross-linker that is reactive to at least one of the components. The components begin cross-linking when they are mixed. The components can be applied separately to the site of administration or the components can be pre-mixed immediately before administration. This hydrogel could be used for purposes such as drug delivery and bioadhesion.

Sehl et al. (U.S. Pat. No. 6,833,408) disclose a hydrogel composed of a cross-linkable polynucleophilic component, a cross-linkable polyelectrophilic component and a hydrophilic polymer. The hydrophilic polymer could be a synthetic or natural polymer, such as fibrin or collagen. The components begins cross-linking upon mixing and might be applied as a surgical adhesive.

Stile & Healy (Biomacromolecules, 2001, 2(1): 185-194) describe a peptide-modified hydrogel composed of N-isopropylacrylamide, diaminopoly(ethylene glycol) and acrylic acid. The acrylic acid component was covalently functionalized with two different peptide sequences that are found in bone sialoprotein.

Kim & Healy (Biomacromolecules, 2003, 4(5): 1214-1223) describe a peptide-modified hydrogel composed of N-isopropylacrylamide, acrylic acid and cross-linker. The cross-linker contained a peptide sequence, which can be cleaved by a collagen-specific matrix metalloproteinase. Both of these hydrogels are said to be injectable at room temperature and formed viscoelastic solids at physiological temperatures.

Li et al. (Biomaterials, 2005, 26: 3093-3104) describe a collagen-based hydrogel copolymer composed of N-isopropylacrylamide, acrylic acid, acryloxysuccinimide and collagen. The characteristics of the hydrogel were quantified, such as pore size, optical clarity, stress measurements and surface topography. Cured hydrogels were implanted into the pig corneas and removed for analysis.

Rosenblatt et al. (U.S. Pat. No. 5,807,581) disclose a collagen-based hydrogel including collagen, a cross-linking agent and polymer of the same charge as collagen. The hydrogel begins to cross-link when the components are mixed. The hydrogel could be injected when still fluid and allowed to finish cross-linking in situ, or the hydrogel could be cross-linked before implantation. The hydrogel matrix could be used in various ways to deliver drugs, such as enclosed within the hydrogel pores, tethered to the polymer of the hydrogel or engulfed in liposomes.

Ulbrich et al. (U.S. Pat. No. 5,124,421) disclose a degradable hydrogel composed of a monovinyl hydrophilic monomer and a divinyl cross-linker. The monovinyl monomer can be copolymerized with other hydrophobic monomers. The cross-linker is based on the structure N,O-dimethacryloylhydroxylamine, where this cross-linker forms covalent bonds and then degrades by hydrolysis.

Lee & Vernon (Macromol. Biosci. 2005, 5(7):629-635) describe a degradable hydrogel composed of N-isopropylacrylamide, acrylic acid and 2-hydroxyethyl methacryl lactacte. The gelation temperature of the hydrogel depended on the ratio of the monomers. Degradation of the hydrogel occurred through hydrolysis of the 2-hydroxyethyl methacryl lactacte component of the hydrogel.

Cha et al. (U.S. Pat. No. 5,702,717) disclose a thermosensitive poly(ether-ester) block copolymer composed of a hydrophobic polymer and a hydrophilic polyethylene glycol polymer. Jeong et al. (U.S. Pat. No. 6,841,617) disclose a thermosensitive aqueous polymer solution composed of a polyethylene glycol block and a biodegradable polyester block. The thermoresponsiveness results from combining two blocks within the copolymer, where each block alone cannot provide thermosensitivity.

A need exists for versatile biocompatible polymer compounds that can serve as cell growth substrates, for drug delivery purposes and generally for use in patients.

SUMMARY

Provided herein are thermoresponsive and biodegradable elastomeric materials, namely copolymers and compositions and structures, such as hydrogels, comprising the copolymers. The copolymers remain fluid at and below room temperature, solidify at physiological temperature, and bind to biological molecules. The copolymers also degrade and dissolve at physiological conditions in a time-dependent manner, which is important for removal of the hydrogel after the applied surgical or medical procedure. The copolymer and its degradation products are biocompatible, for example and without limitation, they are not cytotoxic.

According to one embodiment, the copolymer comprises an N-isopropylacrylamide residue (an N-isopropylacrylamide monomer incorporated into a polymer), one or both of an acrylic acid residue and a methacrylic acid residue and an acrylic residue having an amine-reactive group. The copolymer comprises a polyester linkage in its backbone. According to one non-limiting embodiment, the copolymer is prepared from at least five components: N-isopropylacrylamide or an N-alkyl acrylamide in which the alkyl is methyl, ethyl, propyl, isopropyl or cyclopropyl, acrylic acid and/or methacrylic acid, an acrylic monomer having an amine-reactive group (such as acrylic N-hydroxysuccinimide ester), collagen and a polyester macromer. For example and without limitation, the polyester macromer is a polylactide macromer, comprising hydroxyethyl methacrylate residues and varying numbers of lactide units/residues. In another non-limiting example, the polyester macromer is a poly(trimethylene carbonate macromer), comprising hydroxyethyl methacrylate residues and varying numbers of trimethylene carbonate units/residues. Each component contributes to the desired physical properties of the hydrogel to enable an injectable material for delivering drugs or chemicals, encapsulating and transplanting cells, and injecting into empty cavities for wounds or tissue repair. The amine-reactive component of the copolymer (for instance, acrylic N-hydroxysuccinimide ester) binds to amine-containing compounds including biomolecules such as collagen and/or other bioactive or biocompatible materials or factors. The composition of each component in the hydrogel determines the lower critical solution temperature (LCST) of the hydrogel. At a temperature less than the LCST, the hydrogel flows easily and can be injected into the desired shape. When the temperature is increased above the LCST, the hydrogel solidifies and retains the shape. Once solidified, the hydrogel is highly flexible and relatively strong at physiological temperature.

According to one embodiment, polyester component within the macromer introduces the degradability and hydrophobicity of the copolymer. For complete removal of the copolymer, the copolymer includes hydrolytically-cleavable bonds that results in soluble, non-toxic by-products, even above the LCST of the non-degraded copolymer. Once the copolymer is degraded, the LCST is above physiological temperature, which results in dissolution of the degraded hydrogel and clearance of the degraded components.

Therefore, provided herein is a copolymer comprising an N-alkyl acrylamide residue in which the alkyl is methyl, ethyl, propyl, isopropyl or cyclopropyl, such as N-isopropylacrylamide residue, one of an acrylic acid residue and a methacrylic acid residue and an acrylic residue having an amine-reactive group, the copolymer comprising a biodegradable polyester linkage in its backbone. In one non-limiting embodiment, the amine-reactive group is a succinimide group, an oxysuccinimide group or an isocyanate group. In one embodiment, the copolymer has a lower critical solution temperature below 37° C., in another between 30° C. and 34° C. and in another, less than 27° C. According to one embodiment, the copolymer has a lower critical solution temperature above 37° C. after its ester bonds are hydrolyzed.

To facilitate the hydrolysis of the copolymer, according to one embodiment, the backbone of the polymer comprises biodegradable ester linkages, for example and without limitation, from 1% to 10% of the linkages of the copolymer backbone. The polymer may comprise a polyester macromer, for example and without limitation, a polyester macromer comprising hydroxyethyl methacrylate and lactide residues.

In one embodiment, the ratio of hydroxyethyl methacrylate and lactide residues in the polyester macromer is from 1:2 to 1:8, in another, from 1:1 to 1:10, such as 1:1, 1:2, 1:3, 1:4, 1:5, 1:6, 1:7, 1:8, 1:9, and 1:10. In another non-limiting example, the polyester macromer comprises hydroxyethyl methacrylate and trimethylene carbonate residues. In one embodiment, the ratio of hydroxyethyl methacrylate and trimethylene carbonate residues in the polyester macromer ranges from 1:1 to 1:10, 1:2 to 1:5 or any increment within those ranges, including 1:1, 1:2, 1:3, 1:4, 1:4.2, 1:5, 1:6, 1:7, 1:8, 1:9, and 1:10. Amine-containing biomolecules or other compounds, such as proteins, carbohydrates, glycoproteins, etc. can be conjugated to the copolymer through the amine-reactive group. In certain embodiments, collagen, heparin or gelatin are suitable compounds, for instance and without limitation, between 1% wt and 10% wt collagen. In one embodiment, the copolymer comprises caprolactone, glycolide or trimethylene carbonate residues.

A composition comprising the copolymer described herein and an aqueous solvent, for example and without limitation, water, saline and phosphate-buffered saline also is provided. The composition also can include an active agent, such as, without limitation, one or more of an antiseptic, an antibiotic, an analgesic, an anesthetic, a chemotherapeutic agent, a clotting agent, an anti-inflammatory agent, a metabolite, a cytokine, a chemoattractant, a hormone, a steroid, a protein and a nucleic acid. In one embodiment, where the composition comprises a clotting agent, one example of a clotting agent is desmopressin. A biological material, such as a cell or a virus particle may also be incorporated into the composition.

A method is provided of making a thermosensitive copolymer, for example and without limitation, a co-polymer described herein, the method comprising co-polymerizing N-isopropylacrylamide, acrylic acid and/or methacrylic acid, an acrylic monomer having an amine-reactive group and a polyester linkage-containing monomer to make a copolymer comprising an acrylic and polyester backbone. The monomers can be co-polymerized by any useful polymerization method, for example and without limitation by free-radical polymerization. In one instance, the polyester linkage-containing monomer is a polyester macromer, for example and without limitation, prepared from hydroxyethyl methacrylate and lactide. In one embodiment, the ratio of hydroxyethyl methacrylate and lactide residues in the polyester macromer is from 1:2 to 1:8 or from 1:1 to 1:10. In another non-limiting example, the polyester macromer is prepared from hydroxyethyl methacrylate and trimethylene carbonate. In another instance, the polyester linkage-containing monomer is one of a caprolactone, a glycolide and a trimethylene carbonate monomer.

According to another embodiment a method of growing cells is provided, comprising introducing cells into a copolymer composition described herein to produce a cell construct and incubating the cell construct under conditions suitable for growth of the cells. The composition can comprise cell growth media to facilitate cell growth within the composition. The cell construct can be administered to a patient (placed in a patient's body at a desired location), such as a human patient. In another embodiment, the composition is administered to a patient without cells, but so that the patient's cells migrate into the composition. The composition can be administered by a subcutaneous injection into the desired site within the patient. To facilitate this, the composition may comprise one or more of a cytokine, a cell growth or differentiation agent and a metabolite. The composition also may include an active agent, such as, without limitation, an antiseptic, an analgesic, an anesthetic and an antibiotic. As above, the copolymer can be conjugated with collagen, for example and without limitation, between 0% and 10% by weight of the copolymer of collagen.

BRIEF DESCRIPTION OF THE DRAWINGS

FIG. 13A are photographs of the hydrogel at 37° C. (top), stretched at 37° C. (middle), and recovered after the stretching at 37° C. (bottom). FIG. 13B are photographs of the hydrogel at 37° C. (top), stretched at 37° C., followed by a decrease of temperature to 22° C. leading to fracture of the hydrogel, and completely dissolved at a temperature of 4° C. (bottom).

FIG. 35A is a photograph of the liquid copolymer at 4° C., where FIG. 35B is a photograph of the solid copolymer at 37° C. FIG. 35C is a photograph of the copolymer before stretching, where FIG. 35D is a photograph of the copolymer after stretching.

FIG. 36A shows the tensile strength for these copolymers, where FIG. 36B shows the elongation at break.

FIG. 37A shows the injection site. FIG. 37B shows the sub-cutaneous tissue at the injection site. FIG. 37C shows the sub-fascia tissue at the injection site.

FIG. 38A shows the injection site (indicated by black arrow). FIG. 38B shows the tissue surrounding the injection site (indicated by black arrows).

DETAILED DESCRIPTION

Figure 1:
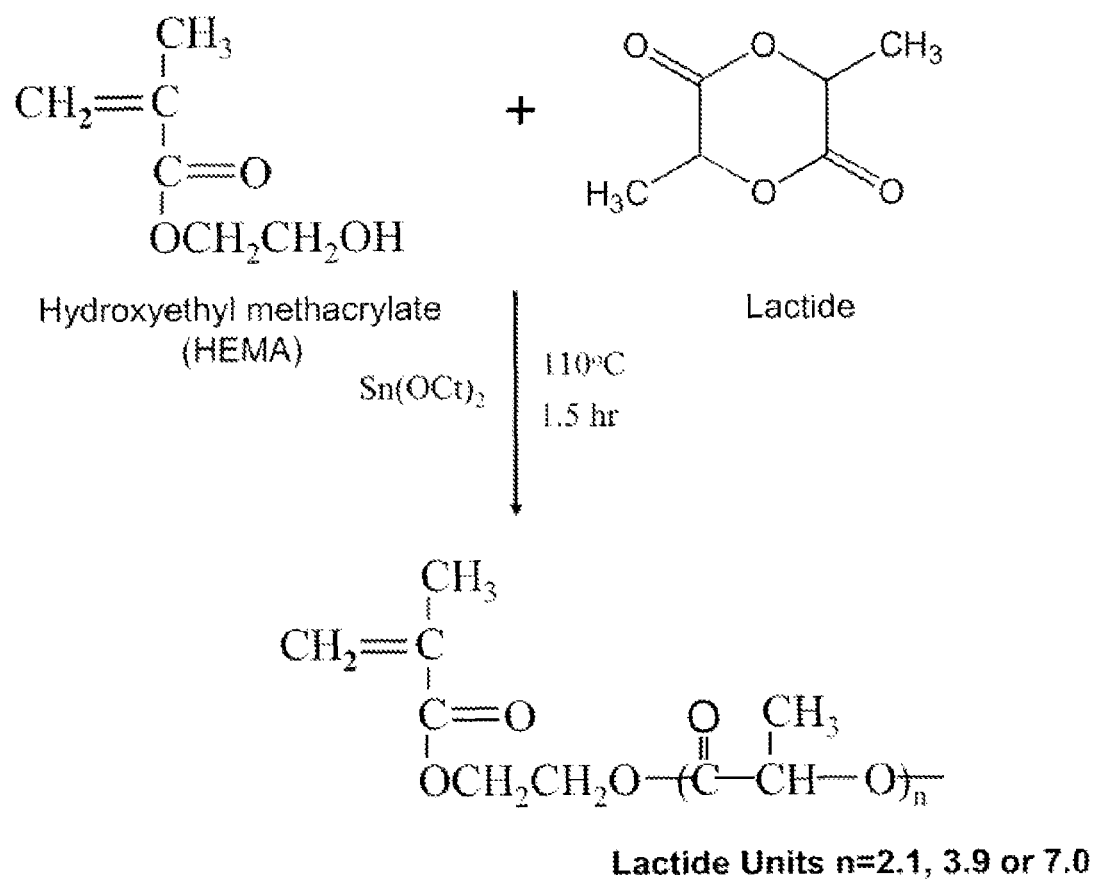
FIG. 1 is a schematic drawing for the synthesis of the polylactide hydroxyethyl methacrylate-lactide (HEMAPLA) macromer from hydroxyethyl methacrylate (HEMA) and lactide (LA).

According to embodiments of the compounds and compositions described herein, provided herein are injectable hydrogels that are biodegradable, elastomeric and thermoresponsive and which can easily take the shape of a cavity into which they are injected in advance of phase transition to solid. The copolymers are injectable as a liquid at or below room temperature (about 25° C.) and are solid at body temperature (about 37° C.). These materials are useful for a number of purposes. For example, in treatment of patients, they may be used as an injectable stem cell niche for bone marrow transplants or for other transplantation settings; delivery vehicles for chemotherapy to tissue, such as, for example and without limitation, gut following tumor resections; sealants for pulmonary and neural applications as well as for emergency treatment of wounds. The materials also can find use as bulking agents for cosmetic applications or, even more generally, rheology modifiers.

According to certain embodiments, copolymers comprise four types or subunits/residues: 1) N-alkyl acrylamide in which the alkyl is methyl, ethyl, propyl, isopropyl or cyclopropyl, for example N-isopropylacrylamide, as a thermosensitive component after polymerization; 2) acrylic acid N-hydroxysuccinimide ester for conjugation of biomolecules; 3) acrylic acid for improvement of hydrophilicity and 4) polyester macromer for introduction of degradability and hydrophobicity. The hydrophobic units of the polyester macromer, for example and without limitation, the lactide units or trimethylene carbonate units, decrease the LCST of the copolymer to well below 37° C. before degradation. After degradation, it forms hydrophilic poly (hydroxyethyl methacrylate) structure in the backbone, which increases hydrophilicity of the polymer, LCST is then increased to above 37° C.

As used herein, the terms "comprising," "comprise" or "comprised," and variations thereof, in reference to elements of an item, composition, apparatus, method, process, system, etc. are meant to indicate that the item, composition, apparatus, method, process, system, etc. includes those elements and that other elements can be included and still fall within the scope/definition of the described item, composition, apparatus, method, process, system, etc. Thus, as a non-limiting example, an apparatus or method that includes elements A, B, C and D may be said to fall within the scope/definition of the apparatus or method said to "comprise" elements A, B and C.

The copolymers, compositions and components thereof are preferably biocompatible. By "biocompatible," it is meant that a polymer composition and its normal in vivo degradation products are cytocompatible and are substantially non-toxic and non-carcinogenic in a patient within useful, practical and/or acceptable tolerances. By "cytocompatible," it is meant that the copolymers or compositions are substantially non-toxic to cells and typically and most desirably can sustain a population of cells and/or the polymer compositions, devices, copolymers, and degradation products thereof are not cytotoxic and/or carcinogenic within useful, practical and/or acceptable tolerances. For example, a copolymer composition when placed in a human epithelial cell culture does not adversely affect the viability, growth, adhesion, and number of cells. In one non-limiting example, the co-polymers, compositions, and/or devices are "biocompatible" to the extent they are acceptable for use in a human veterinary patient according to applicable regulatory standards in a given legal jurisdiction. In another example the biocompatible polymer, when implanted in a patient, does not cause a substantial adverse reaction or substantial harm to cells and tissues in the body, for instance, the polymer composition or device does not cause necrosis or an infection resulting in harm to tissues organs or the organism from the implanted compositions.

As used herein, a "polymer" is a compound formed by the covalent joining of smaller molecules, which are referred to herein as residues, or polymer subunits, when incorporated into a polymer. A "copolymer" is a polymer comprising two or more different residues. Prior to incorporation into a polymer, the residues typically are described as monomers. Non-limiting examples of monomers, in the context of the acrylic/polyester copolymer described herein, include: acrylic or acrylamide monomers, such as acrylic acid, acrylic N-hydroxysuccinimide ester and hydroxyethyl methacrylate, lactide, and trimethylene carbonate. A monomer may be a macromer prepared from even smaller monomers, such as the hydroxyethyl methacrylate-polylactide (HEMAPLA) macromer or the hydroxyethyl methacrylate-poly(trimethylene carbonate) (HEMAPTMC) macromer described herein.

As used herein, an acrylic monomer has the general structure (CH2=CH—C(O)—R), and, when polymerized, forms the general polymer structure having an alkylene backbone ( . . . C—C—C—C—C . . . ) and the overall structure: . . . C—(—C(C(O)R)—C—)$_n$—C(C(O)R)—C . . . in which each instance of R can be the same, or in the case of a copolymer, independently different:

Polyester polymer backbones are polymer backbones containing two or more ester groups. A polyester linkage has an average of more than one ester units (—C(O)O—), as opposed to an ester linkage that has one ester unit. An example is a polylactide macromer as described herein. Another example is a poly(trimethylene carbonate) macromer. Other examples of residues that comprise ester linkages include, without limitation, caprolactones, glycolides and a trimethylene carbonate residues.

Polyester macromers are compounds containing on the average one or more, and preferably two or more ester linkages. In the context of macromer and polymer preparations, unless otherwise indicated, the number of residues indicated as being present in a given polymer or macromer is an average number and is not to be construed as an absolute number. Thus, as a non-limiting example, in the context of the HEMA-PLA macromers, the numbers 2.1, 3.9 and 7.0 refer to an estimated average number of —C(O)—C(CH$_3$)—O— residues present in the macromers in the macromer composition, and, when incorporated into a copolymer, the average number of —C(O)—C(CH$_3$)—O— residues present in the incorporated polyester macromer residues, for example as shown in the Examples below. The average number of residues may be determined by any method, for example and without limitation, by $^1$H-NMR, as in the examples, below.

Lower critical solution temperature (LCST) refers to the temperature below which the constituents of the hydrogel are soluble in water and above which the constituents are insoluble. When the LCST is reached, the polymer constituents in an aqueous solution will aggregate to form hydrogel. The LCST can be determined by measuring the change in transmittance with a UV-Vis spectrometer as a function of temperature (Advanced Drug Delivery Reviews (1998), 31: 197-221 and Annals N.Y. of Science, 1999, 875(1):24-35). LCST also can be determined by any other useful method—for example and without limitation by Differential Scanning Calorimetry (DSC). DSC is used to measure LCTS in the examples below.

One unique aspect of the polymers described herein is that the LCST of these polymers is typically between 18° C. and about 37° C. so that the polymer can be distributed through the marketplace, stored and administered to a patient as a liquid at ambient temperatures (or, if necessary, maintained at a cool temperature with an ice-pack, refrigerator or other cooling device), and the polymer gels as it warms past its LCST. Many polymers suitable for administration to patients require mixing of monomers immediately prior to use, which is undesirable for many reasons. For instance, it is impractical to ask doctors, nurses or technicians to mix monomers as they need the polymer. Further, monomers can have varying degrees of toxicity. The copolymers described herein do not require conducting a chemical reaction at the site of use and the copolymers can be washed free of monomer contamination prior to distribution in the marketplace. Lastly, the release of a portion of the aqueous phase during phase transition can facilitate local drug delivery in the excluded aqueous phase.

Another desirable physical quality of the polymers described herein is that, when ester linkages in the backbone are hydrolyzed (for instance over time in situ in a living system, such as a human patient), the released copolymer fragments have an LCTS above 37° C., so that they are soluble (and as an additional benefit, non-toxic), facilitating safe degradation and clearance of the polymer over time in a living system such as a human body.

In one embodiment, the copolymer comprises an N-isopropylacrylamide residue, one or both of an acrylic acid residue and a methacrylic acid residue (CH$_2$=C(CH$_3$)C(O)OH, an acrylic residue having an amine-reactive group, the copolymer having polyester linkages in its backbone. The copolymer may be reacted with amine-containing compositions, such as compositions or molecules comprising amine groups, for example and without limitation, collagen, fibrin, gelatin and heparin. The polyester linkages may be incorporated in the copolymer backbone by introduction of, for example and without limitation, one or more of a polyester macromer, a polycaprolactone, a polyglycolide and a poly(trimethylene carbonate) into the copolymer. A polyester linkage is a linkage having an average of more than one ester groups which are contributed to the copolymer backbone. In certain non-limiting examples, the polyester linkages are introduced into the copolymer as a polyester macromer, such as a macromer comprising hydroxyethyl methacrylate and lactide residues. Monomers (including as a group macromers) containing ester linkages can be introduced into the copolymer by radical polymerization, or in any useful manner using any suitable initiator, such as benzoyl peroxide.

In one non-limiting example in which the copolymer comprises a macromer comprising hydroxyethyl methacrylate and lactide residues, the ratio of hydroxyethyl methacrylate and lactide residues in the polyester macromer is from 1:1 to 1:10, such as 1:1, 1:2, 1:3, 1:4, 1:5, 1:6, 1:7, 1:8, 1:9, and 1:10. In another non-limiting embodiment, the ratio of hydroxyethyl methacrylate and lactide residues in the polyester macromer is from 1:2 to 1:8. In another non-limiting example in which the copolymer comprises a macromer comprising hydroxyethyl methacrylate and trimethylene carbonate residues, the ratio of hydroxyethyl methacrylate to trimethylene carbonate residues in the polyester macromer ranges from 1:1 to 1:10, 1:2 to 1:5 or any increment within those ranges, including 1:1, 1:2, 1:3, 1:4, 1:4.2, 1:5, 1:6, 1:7, 1:8, 1:9, and 1:10. In one embodiment of the copolymer useful in humans or animals, the copolymer has a lower critical solution temperature below 37° C. For veterinary applications, the LCST can be slightly higher as the core body temperature of certain animals (e.g., cats, dogs, horses, cows, sheep and goats) is in the range of 38° C.-39° C. In another embodiment, the copolymer has a lower critical solution temperature above 37° C. after its backbone ester linkages are hydrolyzed (substantially hydrolyzed, as with treatment of the polymer with NaOH, as described herein).

Amine-reactive groups are groups that react with amine residues, such as Lys residues of proteins, to form a covalent linkage. Non-limiting examples of amine-reactive groups are succinimide, oxysuccinimide or isocyanate groups. Non-limiting examples of useful acrylic monomers include, NHS (shown herein, for example in FIG. 4) and N-acryloxysuccinimide ester, having the structure:

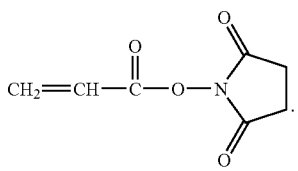

In medical or veterinary uses, the copolymers and compositions comprising the copolymers may serve as adhesives or fillers. They may be applied to wounds or into body cavities or used as a tissue packing to apply compression. As such, embodiments of the copolymer solutions described herein may be applied to wounds and, in one embodiment covered, optionally with a warming compress or "heat pack" as are available commercially to ensure that the copolymer is maintained at a temperature above its LCST and thus remains gelled when in contact with any cooler areas of the body, typically the skin. As a hydrogel, embodiments of the copolymers disclosed herein may be contained in a composition comprising the copolymer and an aqueous solution that does not interfere substantially with the LCST and polymer structure in its intended use. For instance, the composition may comprise any aqueous solvent, optionally pharmaceutically acceptable, including, without limitation, water, PBS, Saline, etc. As used herein, and "aqueous solvent", is an aqueous solution compatible with the copolymer which can be absorbed into the copolymer matrix. The composition also may comprise an active agent, biological or drug, such as, without limitation: antibiotics, clotting agents (without limitation, an antifibrinolytic, such as desmopressin/DDVAP), analgesics, anesthetics, antiseptics, anti-inflammatory agents, chemotherapeutic agents, metabolites, rheology modifiers, cytokines, chemoattractants, hormones, steroids, proteins (including enzymes), nucleic acids, cells, virus particles, nucleic acids, biomatrices or precursors thereof, or a foaming agent. In one embodiment, the composition comprises stem cells (such as adipose-derived stem cells) or other progenitor cells so that the composition is useful as a biodegradable tissue engineering scaffold. The composition, even without cells, is useful as a cell growth niche or scaffolding into which cells such as native stem/progenitor cells can migrate in situ. In such an embodiment, chemokines, cellular growth agents and cellular differentiation agents can be included within the composition to attract cells into the composition and promote cellular growth and differentiation when placed in situ.

According to one embodiment, in its application to wound treatment, a clotting agent such as desmopressin may be included in a polymer composition. An appropriate, e.g., pharmaceutically acceptable, foaming agent as are well-known in the relevant arts also may be included for the purpose of creating compression in a wound, whether exposed to a body surface in the case of (for example) puncture wounds or bullet wounds, or internal wounds, in which case, the polymer can be injected into or near a site of internal bleeding. As such, the composition can find use in many situations, ranging from home use to stabilization of bleeding or massively bleeding patients in emergency and battlefield situations. The copolymer also can be used during surgical procedures to apply compression and otherwise secure a site of injury, such as a portion of a patient's intestine, nasal passage or sinus cavity where a tumor or polyp has been removed or after other surgeries. The benefits of such a reversibly-gelling copolymer composition is that the composition can be removed simply by cooling, for example and without limitation, by flushing with cool (lower than the copolymer's LCST) flushing solution, such as water, saline or phosphate-buffered saline. Thus, while a wound and bleeding in a patient can be stabilized by application of the polymer, the polymer can be selectively eroded in an emergency room or during surgery simply by flushing with a cool (for example and without limitation, 0° C. to 30° C.) saline solution.

In a further embodiment, the composition serves as a cell growth medium. According to one embodiment, cells are introduced into a composition comprising a copolymer as described herein to produce a cell construct. The cell construct is incubated under conditions suitable for growth of the cells. That is, the cell construct can be placed in an incubator or into a patient so that the cells are maintained under adequate environmental conditions to permit the cells to survive, proliferate, differentiate and/or express certain products. "Cell growth" means that the cells survive and preferably, though not exclusively, divide and multiply. The composition may comprise cell growth media, which typically provides necessary nutrients and environmental conditions for cell growth. The cells may be introduced and incubated under conditions suitable for cell growth by introducing the composition into a patient and allowing native cells, such as stem cells to migrate into the composition. The composition can be administered by injecting the composition into the region requiring cellular growth or remodeling, such as a region of damaged tissue. In one non-limiting example, the damaged tissue is within the cardiac wall caused by a myocardial infarction and the composition is injected into the cardiac wall. In one variation of that embodiment, cytokines, chemoattractants, nutrients and/or cell differentiation factors are included in the composition. The composition may also contain one or more of an antiseptic, an analgesic, an anesthetic and an antibiotic (for example, for selection of the cells or to prevent bacterial growth in the composition). To facilitate cell growth, in one non-limiting embodiment, the copolymer is conjugated with collagen, for example between 0% and 10% by weight of the copolymer of collagen.

Compositions comprising a copolymer described herein can be distributed for use in any suitable vessel. In one instance, the composition is packaged in a sealed container, from which the composition can be poured, squeezed or otherwise decanted, for example and without limitation, by use of a syringe. The vessel can be a bag, such as an IV bag. In another embodiment, the composition can be distributed in a syringe for immediate dispensation into a wound or body cavity/location. A syringe can be fitted with any type of needle, tip, tube, balloon device or other useful fitting for facilitating accurate placement of the solution in or around a desired delivery site, for example and without limitation, for delivery into the large intestine of a patient after removal of a tumor. In another embodiment, the composition and a pharmaceutically acceptable solvent is stored within a syringe at or below 4° C. and the syringe is fitted with a needle gauge sufficient to allow for injection without increased pressure but also prohibit back flow of the solution into the syringe after injection, such as, without limitation, a 16 through 23 G (gauge) needle, and in certain embodiments an 18 G or 20 G needle. Thus, methods of use embodying the above-described uses for a copolymer described herein and compositions comprising the copolymer are contemplated and embraced as part of the present invention.

In another use, a composition described herein can be used for cosmetic purposes, such as for a rheology modifier. Ingredients, including without limitation colorants, fragrances, flavors, and other ingredients listed herein, including active agents, may be included in the composition.

The following examples are provided for illustration purposes and are not intended to limit the scope of the present invention.

EXAMPLES

A hydrogel possessing thermoresponsive behavior coupled with robust mechanical properties suitable for soft tissue engineering is of great interest. Such a thermoresponsive scaffold could readily encapsulate and deliver cells for subsequent mechanical training in vivo or in vitro. Described herein and in the examples below is a family of injectable and flexible hydrogel composites based on thermosensitive copolymers, optionally conjugated with collagen. The molecular structure of the hydrogels was confirmed with FT-IR, 1H-NMR and differential scanning calorimetry. The copolymers showed no cytotoxicity. The composite hydrogels formed effectively when collagen content was less than 10%. In the examples below, a phase transition temperature occurred between 31-33.5° C. and the copolymers absorb 150-205% $H_2O$ at 37° C. depending on copolymer composition and collagen content. The hydrogels had tensile strengths >0.39 MPa and elongations at break >130% at 37° C. Degradation in buffer with or without collagenase at 8 weeks showed 6-17% mass loss at 37° C. In collagen-containing samples, smooth muscle cell adhesion was 60% of tissue culture polystyrene (vs. 35% without collagen) and cell numbers increased over a 2-week culture period. Hydrogels with lower collagen content showed higher cell encapsulation efficiency. In addition, subcutaneous injections of these copolymer solutions were conducted on in vivo porcine models. These novel thermosensitive, biodegradable and flexible hydrogels have properties attractive for future application in soft tissue engineering.

Example 1

Flexible, Injectable and Thermosensitive Poly(NIPAAm-co-AAc-co-NHS-co-HEMAPLA Ester) Hydrogel A thermosensitive copolymer hydrogel has been developed that is injectable at low (e.g. room) temperature, capable of binding biomolecules such as collagen and other bioactive factors (e.g. growth factors, differentiation factors). The copolymer is highly flexible and relative strong for use in soft tissue engineering, characterized by an LCST lower than 37° C. before degradation, such that it can form a gel at body temperature, and characterized by an LCST higher than 37° C. after degradation such that the degradation product(s) can dissolve in the body's aqueous environment and be cleared.

The polymer comprises residues of: N-isopropylacrylamide as thermosensitive component after polymerization; acrylic N-hydroxysuccinimide ester for conjugation of biomolecules; acrylic acid for improvement of hydrophilicity; and polylactide macromer for introduction of degradability and hydrophobicity. The hydrophobic lactide units decrease LCST of the copolymer to well below 37° C. before degradation (hydrolysis). After degradation, it forms hydrophobic poly(hydroxyethyl methacrylate) structure in the backbone, which increases hydrophilicity of the polymer, LCST is then increased to above 37° C.

FIG. 1 illustrates the synthesis of a polylactide hydroxyethyl methacrylate-lactide (HEMAPLA) macromer from hydroxyethyl methacrylate (HEMA) and lactide (LA). Polylactide macromer HEMAPLA was synthesized by ring-open polymerization of lactide with 2-hydroxyethyl methacrylate with stannous octoate as catalyst. Stoichiometric amounts of lactide and 2-hydroxyethyl methacrylate (HEMA) were mixed in a 250 mL three-neck flask. Stannous octoate (1 mol % with respect to HEMA) in 1 mL toluene was added subsequently. Reaction was conducted at 110° C. for 1.5 hours under a nitrogen atmosphere. The mixture was then dissolved in tetrahydrofuran (THF) and precipitated in cool water. The precipitate was collected by centrifugation, dissolved in ethyl acetate and dried with $MgSO_4$ overnight. Ethyl acetate was evaporated under reduced pressure. The yield viscous oil was dried in a vacuum oven overnight. Polylactide macromers with various lactide units were synthesized by altering feed ratio of lactide and HEMA. Polylactide macromers with lactide units 2.1, 3.9 and 7.0 (the average number of lactide units per "macromer") were obtained with lactide:HMEA feed ratios 1, 2 and 4, respectively.

Figure 2:
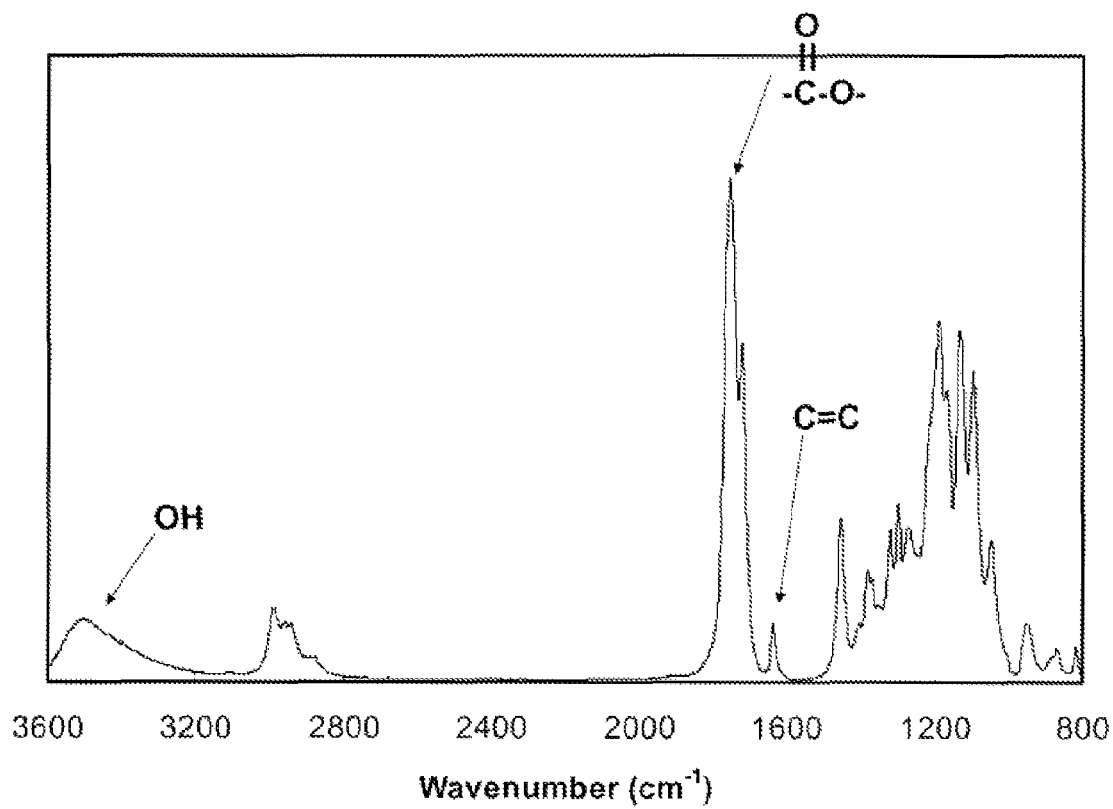
FIG. 2 is an FT-IR spectrum of the HEMAPLA macromer, where absorptions of important functional groups are labeled.

FIG. 2 shows the absorptions of the functional groups of a HEMAPLA macromer (HEMAPLA 2.1) in Fourier Transform Infrared spectrum (FT-IR), where broad and weak carboxylic group absorptions were observed at 1713 $cm^{-1}$, ester group absorption at 1730 $cm^{-1}$, and succinimide group at 1763 $cm^{-1}$ with weak peaks at 1795 and 1812 $cm^{-1}$. FT-IR spectra were obtained at room temperature with a Nicolet FT-IR spectrometer. A 5% solution of polymer in chloroform was placed directly onto the NaCl window with subsequent evaporation of chloroform at 50° C.

Figure 3:
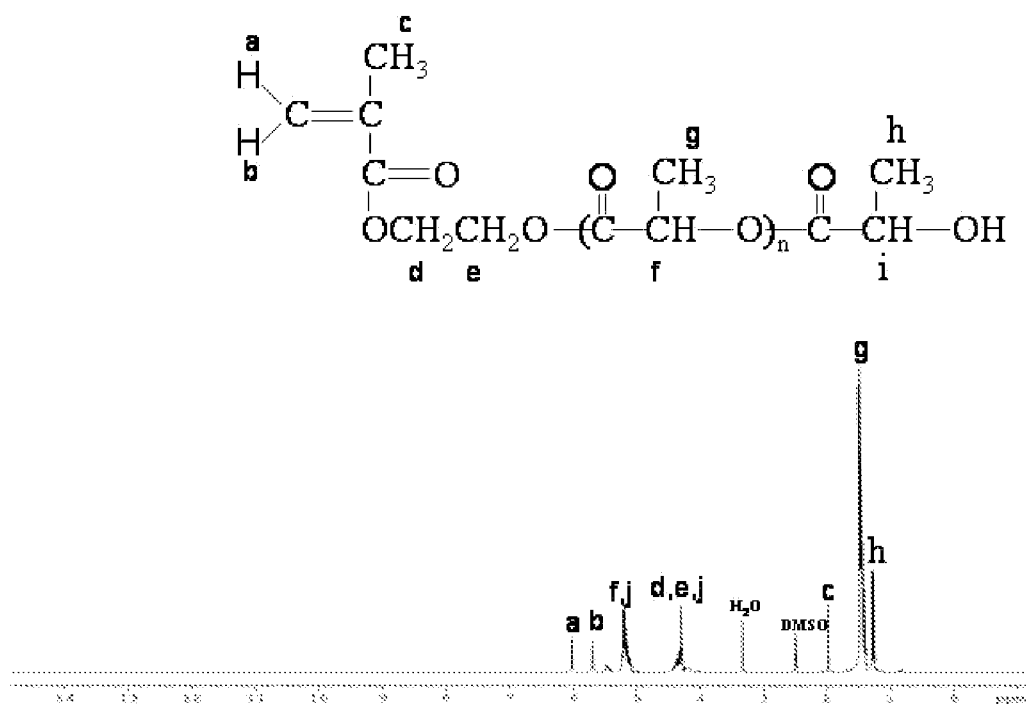
FIG. 3 is a 1H-NMR spectrum of the HEMAPLA macromer, where characteristic peaks of protons are labeled from a to i according to the structure shown.

The $^1$H-NMR of the HEMAPLA 2.1 was obtained. FIG. 3 shows the $^1$H-NMR spectrum that confirms the structure of the HEMAPLA macromer, where the peaks of the protons in the spectra correlate with the corresponding protons labeled from a to i in the structure of HEMAPLA in the figure. The number of lactate units in HEMPLA can be calculated from the ratio of the integrals of the methine in lactate at 5.2 ppm and the double bond in HEMA at 5.7-6.0 ppm. Solvent peaks are shown for $H_2O$ at ~3.3 ppm and for DMSO at ~2.5 ppm. $^1$H-NMR spectra were recorded with a 300 MHz spectrometer using DMSO-$d_6$ as a solvent.

Figure 4:
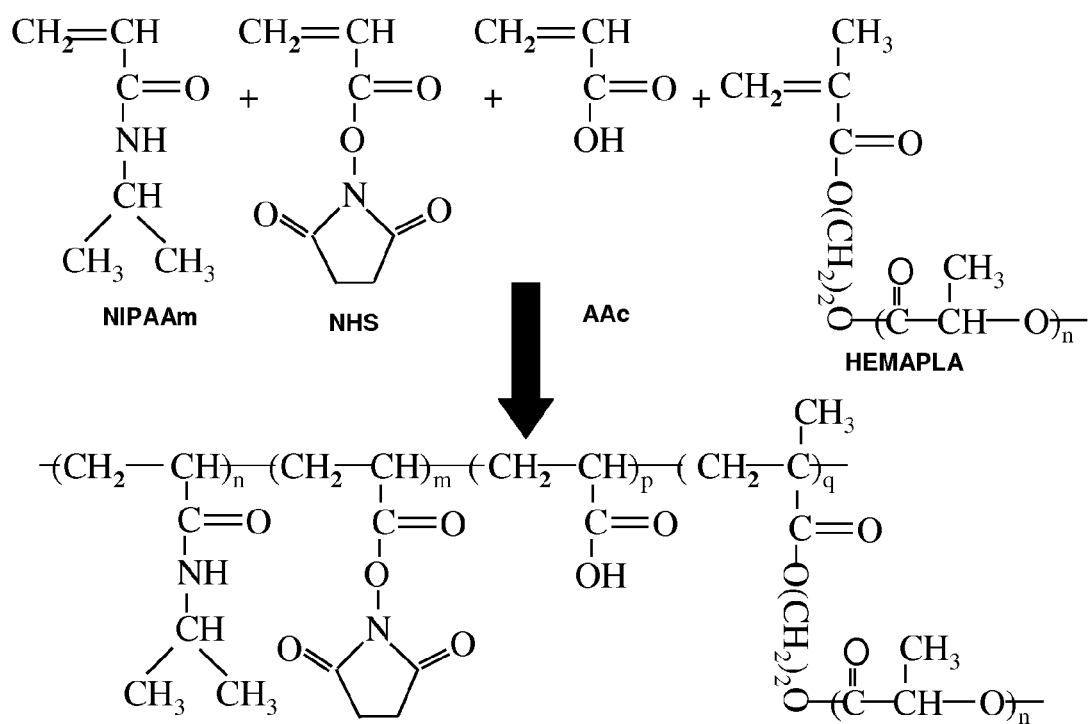
FIG. 4 is a schematic drawing for the synthesis of P(NIPAAm-co-AAc-co-NHS-co-HEMAPLA) copolymer composed of N-isopropylacrylamide (NIPAAm), acrylic acid (AAc), acrylic N-hydroxysuccinimide ester (NHS), and HEMAPLA macromer.

FIG. 4 illustrates the synthesis of the P(NIPAAm-co-AAc-co-NHS-co-HEMAPLA) copolymer, which is composed of N-isopropylacrylamide (NIPAAm), acrylic acid (AAc), acrylic N-hydroxysuccinimide ester (NHS), and HEMAPLA macromer. Copolymers were synthesized by radical polymerization with benzoyl peroxide (BPO) as initiator. Stoichiometric amount of monomers were dissolved in 1,4-dioxane and mixed in a 250 mL one-neck flask under an argon atmosphere for 10 minutes. Degassed BPO ($7.2 \times 10^{-3}$ mol/mol monomer) in 1,4-dioxane solution was then added into the flask. The reaction was carried out at 70° C. for 24 hours. The mixture was cooled to room temperature, precipitated in hexane and filtered. The polymer was dried overnight in a vacuum oven and then purified by repeating dissolving in THF and precipitating with diethyl ether. Table 1 provides the feed ratios and composition (as determined by 1H-NMR) for the resultant copolymers.

TABLE 1

Composition of Poly(NIPAAm-co-NHS-co-AAc-co-HEMAPLA)

| Polymer | Feed ratio | Composition* |
|---|---|---|
| P(NIPAAm-co-AAc-co-NHS-co-HEMAPLA2.1**) | 85/6/5/4 | 85/6.7/3.9/4.4 |
| P(NIPAAm-co-AAc-co-NHS-co-HEMAPLA3.9**) | 85/6/5/4 | 85/6.9/4.0/4.1 |
| P(NIPAAm-co-AAc-co-NHS-co-HEMAPLA7.0**) | 85/6/5/4 | 85/6.9/3.8/4.3 |
| P(NIPAAm-co-AAc-co-NHS-co-HEMAPLA2.1**) | 80/6/5/9 | 80/7.5/4.2/8.3 |
| P(NIPAAm-co-AAc-co-NHS-co-HEMAPLA3.9**) | 80/6/5/9 | 80/7.0/4.4/8.6 |
| P(NIPAAm-co-AAc-co-NHS-co-HEMAPLA2.1**) | 75/6/5/14 | 75/7.3/4.7/13.0 |
| P(NIPAAm-co-AAc-co-NHS-co-HEMAPLA3.9**) | 75/6/5/14 | 75/6.3/4.9/13.8 |
| P(NIPAAm-co-AAc-co-NHS-co-HEMAPLA2.1**) | 80/11/5/4 | 80/11.4/4.2/4.4 |
| P(NIPAAm-co-AAc-co-NHS-co-HEMAPLA3.9**) | 80/11/5/4 | 80/10.6/6.2/3.2 |

*Determined by H1-NMR.
**Lactide units

Figure 5:
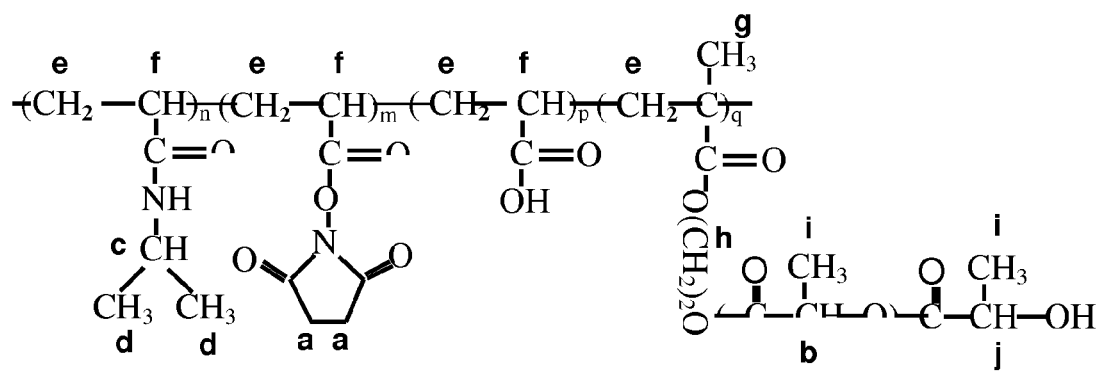
FIG. 5 is the 1H-NMR spectrum of the P(NIPAAm-co-AAc-co-NHS-co-HEMAPLA) copolymer, where characteristic peaks of protons are labeled from a to j according to the structure shown.
Figure 5:
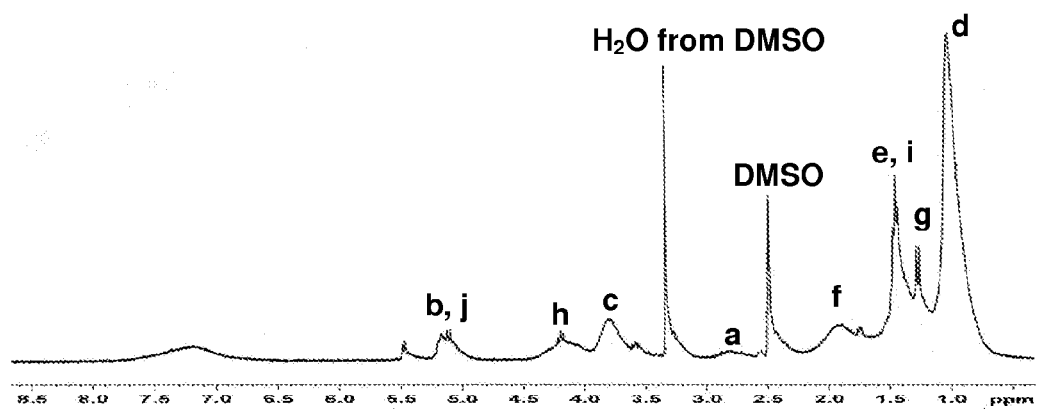

FIG. 5 shows an $^1$H-NMR spectrum that confirms the structure of the P(NIPAAm-co-AAc-co-NHS-co-HEMAPLA) copolymer 85/6/5/4, where the peaks of the protons in the spectra correlate with the corresponding protons labeled from a to j in the structure of HEMAPLA in the figure. Solvent peaks are shown for $H_2O$ at ~3.3 ppm and for DMSO at ~2.5 ppm.

The resultant copolymer was conjugated with collagen. The copolymer was dissolved in PBS (pH=7.4) to 20% wt. Type I collagen solution (4 wt %) was mixed with the copolymer polymer solution at 4° C. Final collagen content was varied from 5% to 20%. To react the NHS residues and collagen, the mixture was incubated overnight at 4° C. Table 2 shows the results of this experiment.

Low Critical Solution Temperature (LCST) was determined by Differential Scanning Calorimetry (DSC-60; Shimadzu) with a scanning rate of 10° C./min over a range of 0 to 80° C. The temperature at the maxima of the endotherm peak was taken as the LCST. LCSTs were determined for polymers after synthesis and after hydrolysis with NaOH, as shown in Table 3. After synthesis, copolymer solutions were formed by dissolving copolymers in PBS (pH=7.4) at 20 wt %. LCSTs of completely hydrolyzed copolymers were measured after hydrolysis in a 1.0 M NaOH solution at 4° C. for 10 days, followed by neutralization with a 10 M HCl solution.

TABLE 2

Hydrogel formation with collagen.

| Polymer | Collagen content (%) | | | |
|---|---|---|---|---|
| | 0 | 5 | 10 | 20 |
| P(NIPAAm-co-AAc-co-NHS-co-HEMAPLA2.1)85/6/5/4 | + | + | + | − |
| P(NIPAAm-co-AAc-co-NHS-co-HEMAPLA3.9)85/6/5/4 | + | + | + | − |
| P(NIPAAm-co-AAc-co-NHS-co-HEMAPLA7.0)85/6/5/4 | + | + | + | − |
| P(NIPAAm-co-AAc-co-NHS-co-HEMAPLA2.1)80/6/5/9 | + | + | + | − |
| P(NIPAAm-co-AAc-co-NHS-co-HEMAPLA3.9)80/6/5/9 | + | + | + | − |
| P(NIPAAm-co-AAc-co-NHS-co-HEMAPLA2.1)75/6/5/14 | + | + | + | − |
| P(NIPAAm-co-AAc-co-NHS-co-HEMAPLA3.9)75/6/5/14 | + | + | + | − |
| P(NIPAAm-co-AAc-co-NHS-co-HEMAPLA2.1)80/11/5/4 | + | + | + | − |
| P(NIPAAm-co-AAc-co-NHS-co-HEMAPLA3.9)80/11/5/4 | + | + | + | − |

"+" Gelation (form hydrogel),
"−" Precipitation (not form hydrogel).

TABLE 3

LCST

| Polymer | After synthesis | After NaOH hydrolysis |
|---|---|---|
| P(NIPAAm-co-AAc-co-NHS-co-HEMAPLA2.1)85/6/5/4 | 26.0 | 41.1 |
| P(NIPAAm-co-AAc-co-NHS-co-HEMAPLA3.9)85/6/5/4 | 25.8 | 41.4 |
| P(NIPAAm-co-AAc-co-NHS-co-HEMAPLA7.0)85/6/5/4 | 24.8 | 42.3 |
| P(NIPAAm-co-AAc-co-NHS-co-HEMAPLA2.1)80/6/5/9 | 24.0 | 41.8 |
| P(NIPAAm-co-AAc-co-NHS-co-HEMAPLA3.9)80/6/5/9 | 21.0 | 42.0 |
| P(NIPAAm-co-AAc-co-NHS-co-HEMAPLA2.1)75/6/5/14 | 19.4 | 41.2 |
| P(NIPAAm-co-AAc-co-NHS-co-HEMAPLA3.9)75/6/5/14 | 18.4 | 40.8 |
| P(NIPAAm-co-AAc-co-NHS-co-HEMAPLA2.1)80/11/5/4 | 26.1 | 60.6 |
| P(NIPAAm-co-AAc-co-NHS-co-HEMAPLA3.9)80/11/5/4 | 26.0 | 61.1 |

TABLE 3-continued

LCST

| Polymer | Collagen content (%) | | |
|---|---|---|---|
| | 0 | 5 | 10 |
| P(NIPAAm-co-AAc-co-NHS-co-HEMAPLA3.9)80/6/5/9 | 21.0 | 21.2 | 22.4 |

Figure 6:
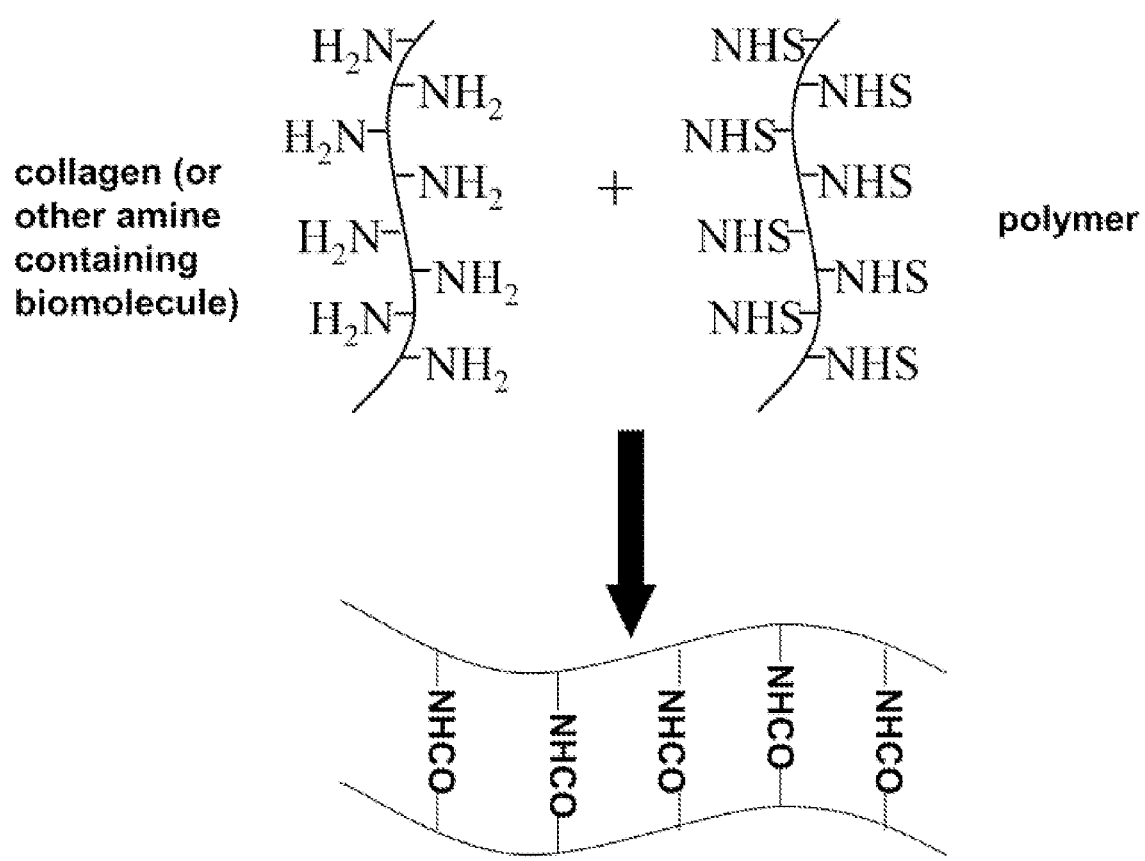
FIG. 6 is a schematic drawing of the conjugation of the copolymer with the anime-containing biomolecule, collagen.
Figure 7A:
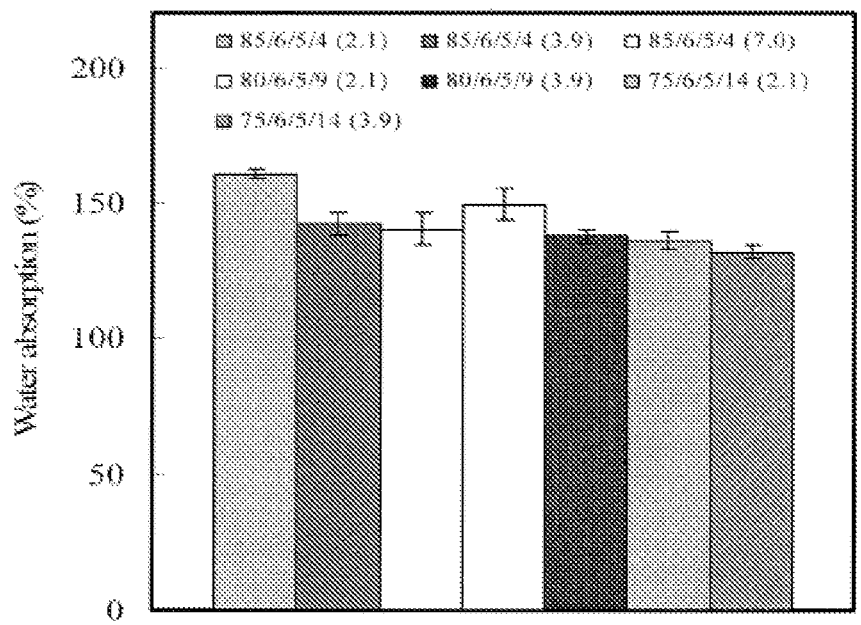
FIG. 7A is a graph quantifying water absorption at 37° C. of P(NIPAAm-co-AAc-co-NHS-co-HEMAPLA) copolymer for various feed ratios of NIPAAm/AAc/NHS/HEMAPLA (LA units), where water absorption rate decreases as the number of LA units in HEMAPLA increases and as the ratio of HEMAPLA in the copolymer increases.
Figure 7B:
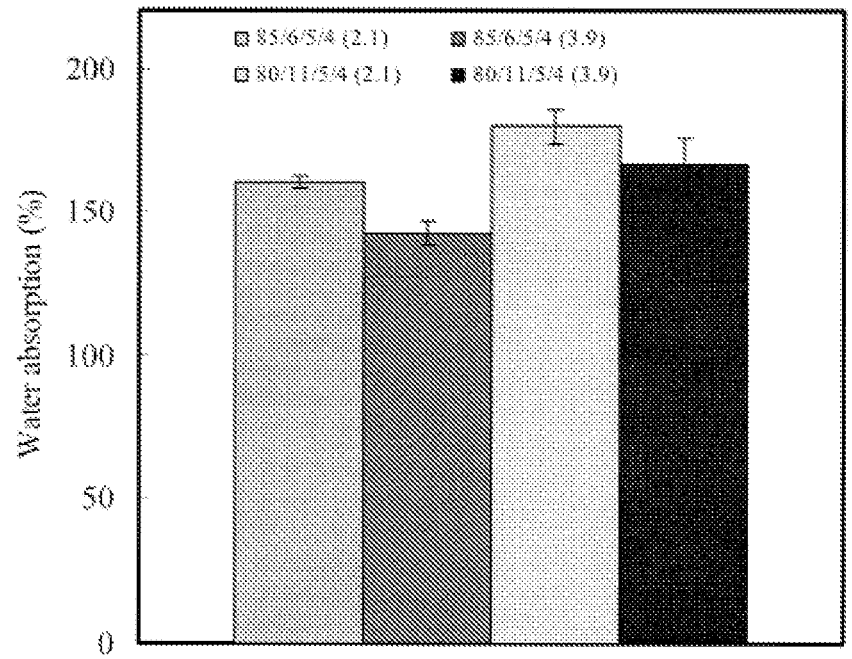
FIG. 7B is a graph quantifying water absorption at 37° C. of copolymers for various feed ratios of NIPAAm/AAc/NHS/HEMAPLA (LA units), where water absorption rate increases as the ratio of AAc in the copolymer increases.

FIG. 6 shows schematically the conjugation of the copolymer with an anime-containing biomolecule, such as collagen, where the amine functional group reacts with the carbonyl group on the NHS unit. FIGS. 7A and 7B show the effect of the various feed ratios of the P(NIPAAm-co-AAc-co-NHS-co-HEMAPLA) copolymer on the water absorption rate. Water absorption rate was measured at 37° C. by mass change of dry and wet samples. Of note, all copolymer hydrogels have water absorption rate greater than 130%. FIG. 7A shows that when the number of LA units in HEMAPLA unit increases from 2.1 to 3.9, then water absorption significantly decreases (p<0.05). Comparing polymers with the same lactate length, the decrease of NIPAAm/HEMAPLA from 85/4 to 75/14 significantly decreased water absorption (p<0.05). FIG. 7B shows that when the ratio of AAc in the copolymer increased from 6% to 11%, the water absorption rate significantly increased (p<0.05).

Figure 8:
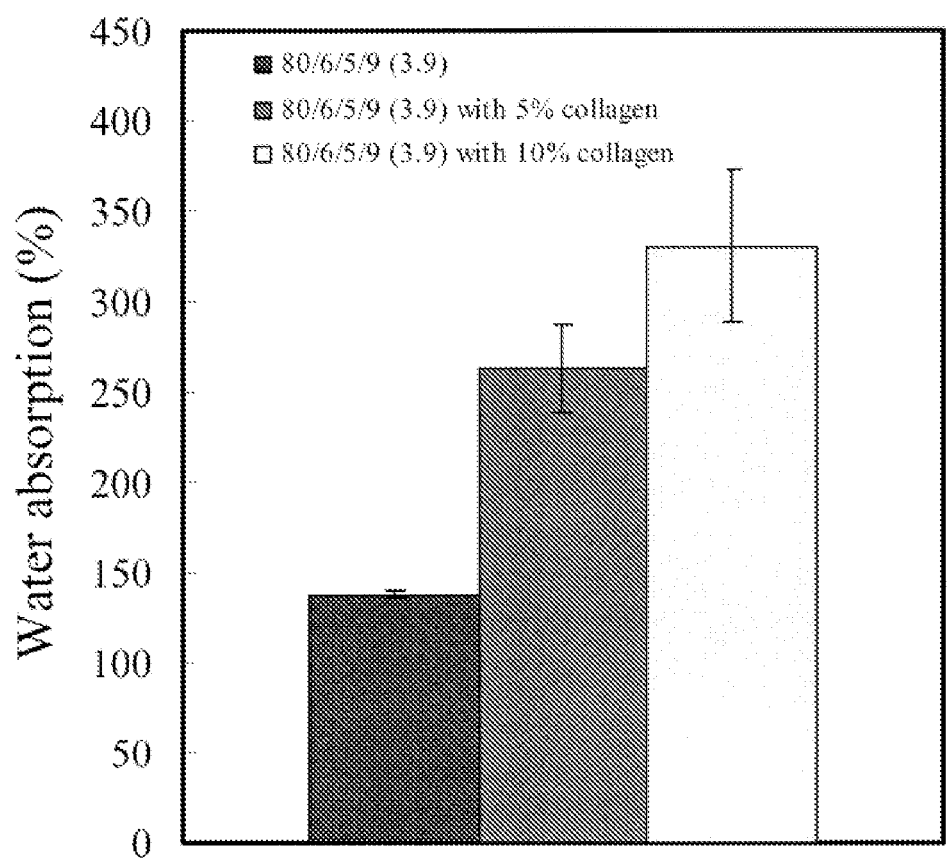
FIG. 8 is a graph quantifying water absorption at 37° C. of the copolymer composed of NIPAAm/AAc/NHS/HEMAPLA (LA units) before and after conjugation with collagen, showing that water absorption rate increases as the collagen content in the hydrogel increases.

FIG. 8 shows the effect of the conjugation of collagen to a P(NIPAAm-co-AAc-co-NHS-co-HEMAPLA) copolymer at a fixed feed ratio of 80/6/5/9 (3.9) on the water absorption rate. After conjugation with collagen, the copolymer absorbs more water (p<0.05).

Figure 9A:
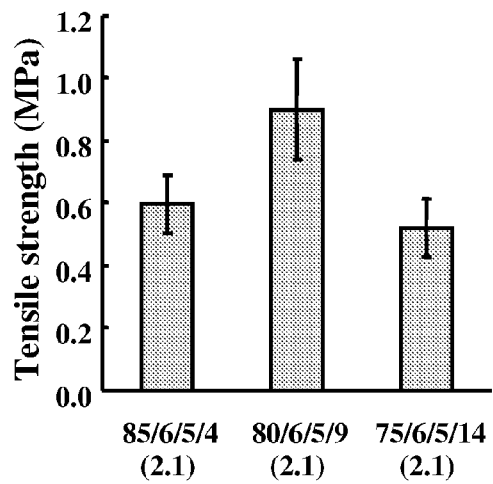
FIG. 9A is a graph quantifying the tensile strength (measured in MPa) at 37° C. of copolymers composed of NIPAAm/AAc/NHS/HEMAPLA (LA units) for various ratios of NIPAAm/HEMAPLA, showing that tensile strength increases as NIPAAm/HEMAPLA initially decreases and then tensile strength decreases as NIPAAm/HEMAPLA further decreases.

FIG. 9A shows the effect of various ratios of NIPAAm:HEMAPLA on the tensile strength (measured in MPa) at 37° C. of P(NIPAAm-co-AAc-co-NHS-co-HEMAPLA) copolymers. Tensile strength was measured by a Universal Testing Machine (Applied Test Systems, with a 5 lb or 10 lb load cell and 10 mm/min tensile speed). Decreasing the NIPAAm/HEMAPLA ration from 85/4 to 80/9 significantly improves tensile strength (p<0.05), while further decreasing the ratio to 75/14 decreased tensile strength (p<0.05).

Figure 9B:
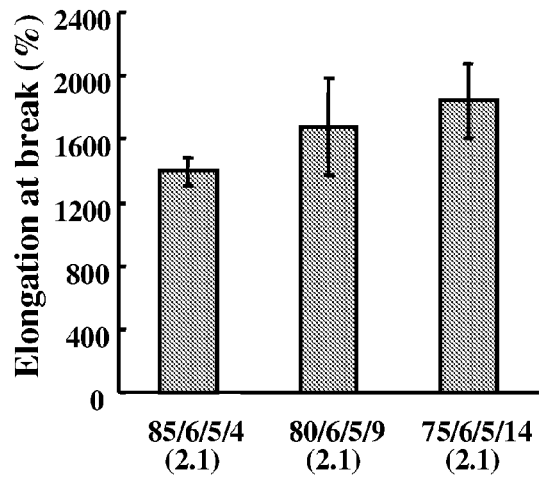
FIG. 9B is a graph quantifying the elongation at break (measured in %) at 37° C. of copolymers composed of NIPAAm/AAc/NHS/HEMAPLA (LA units) for various ratios of NIPAAm/HEMAPLA, showing that elongation at break increases as NIPAAm/HEMAPLA decreases.
Figure 10A:
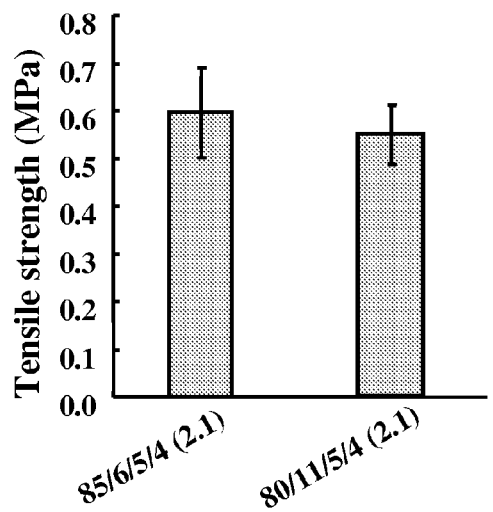
FIG. 10A is a graph quantifying the tensile strength at 37° C. of copolymers composed of NIPAAm/AAc/NHS/HEMAPLA (LA units) for various ratios of NIPAAm/AAc, showing that tensile strength does not change significantly as NIPAAm/AAc decreases.
Figure 10B:
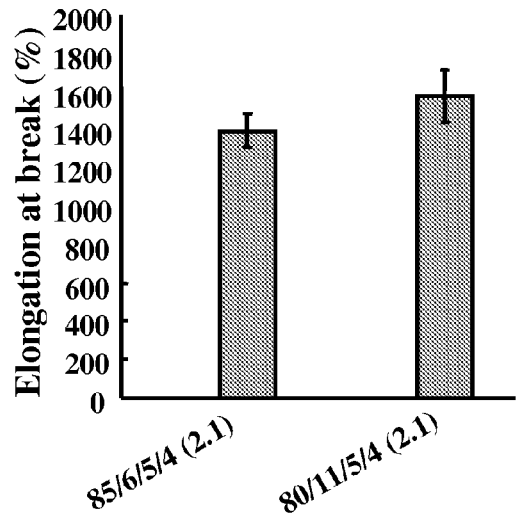
FIG. 10B is a graph quantifying the elongation at break at 37° C. of copolymers composed of NIPAAm/AAc/NHS/HEMAPLA (LA units) for various ratios of NIPAAm/AAc, showing that elongation at break does not change significantly as NIPAAm/AAc decreases.

FIG. 9B shows the effect of various ratios of NIPAAm/HEMAPLA on the elongation at break at 37° C. of P(NIPAAm-co-AAc-co-NHS-co-HEMAPLA) copolymers. Elongation at break is measured by a Universal Testing Machine (Applied Test Systems, 5 lb or 10 lb load cell and 10 mm/min tensile speed). The elongation at break increases as NIPAAm/HEMAPLA decreases (p<0.05 for 85/4 versus 75/14). FIG. 10A illustrates the effect of various ratios of NIPAAm/AAc on the tensile strength (measured in MPa) at 37° C. of P(NIPAAm-co-AAc-co-NHS-co-HEMAPLA) copolymers. The tensile strength does not change significantly as NIPAAm/AAc decreases. FIG. 10B shows the effect of various ratios of NIPAAm/HEMAPLA on the elongation at break at 37° C. of P(NIPAAm-co-AAc-co-NHS-co-HEMAPLA) copolymers. The elongation at break does not change significantly as NIPAAm/AAc decreases. The tensile strength decreased from 0.60±0.10 MPa to 0.55±0.06 MPa when the AAc content was increased from 6% to 11% in copolymers with 85/6/5/4 (2.1) and 85/11/5/4 (2.1) monomer ratios respectively (p>0.05), while the elongation at break increased from 1398±87% to 1580±138% (p>0.04).

Figure 11A:
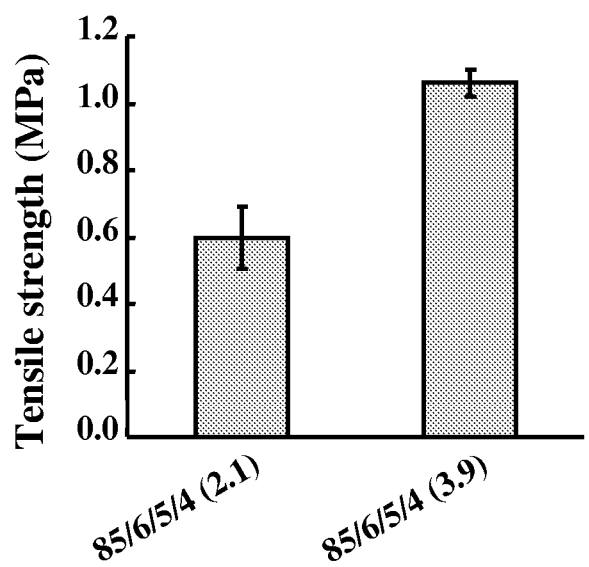
FIG. 11A is a graph quantifying the tensile strength at 37° C. of copolymers composed of NIPAAm/AAc/NHS/HEMAPLA (LA units) for various numbers of LA units in the HEMAPLA macromer, showing that tensile strength increases as the number of LA units increases.
Figure 11B:
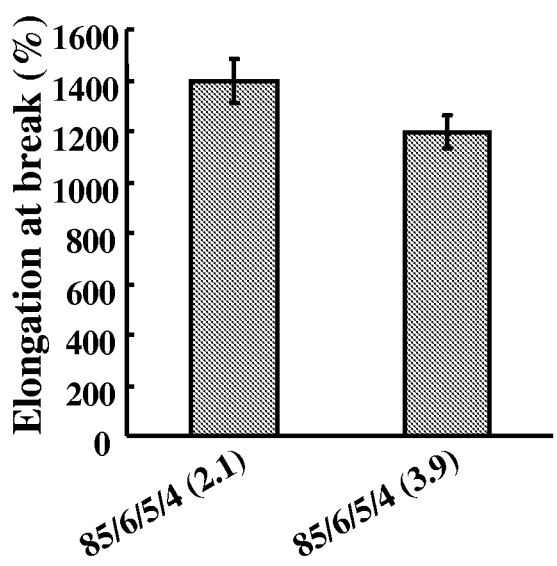
FIG. 11B is a graph quantifying the elongation at break at 37° C. of copolymers composed of NIPAAm/AAc/NHS/HEMAPLA (LA units) for various numbers of LA units in the HEMAPLA macromer, showing that elongation at break decreases as the number of LA units increases.

FIG. 11A shows the effect of the number of LA units in the HEMAPLA macromer on the tensile strength (measured in MPa) at 37° C. of P(NIPAAm-co-AAc-co-NHS-co-HEMAPLA) copolymers. The tensile strength increases as the number of LA units in the macromer increases. FIG. 11B shows the effect of the number of LA units in the HEMAPLA macromer on the elongation at break at 37° C. of P(NIPAAm-co-AAc-co-NHS-co-HEMAPLA) copolymers. The elongation at break decreases as the number of LA units in the macromer increases. At the same NIPAAm/HEMAPLA ratio of 85/6/5/4, increasing the number of lactide units from 2.1 to 3.9 increased the tensile strength from 0.6±0.10 MPa to 1.1±±0.04 MPa (p<0.01), while elongation at break decreased from 1398±87 to 1196±63% (p<0.05).

Figure 12A:
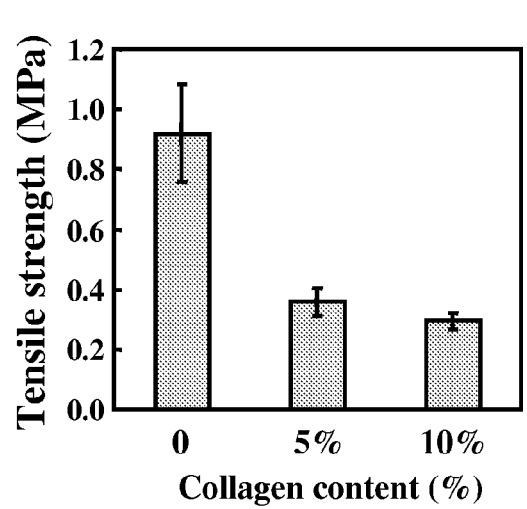
FIG. 12A is a graph quantifying the tensile strength at 37° C. of copolymers composed of NIPAAm/AAc/NHS/HEMAPLA (LA units) for various percentage content of collagen conjugating with the copolymer, showing that tensile strength slightly decreases as the content of collagen increases.
Figure 12B:
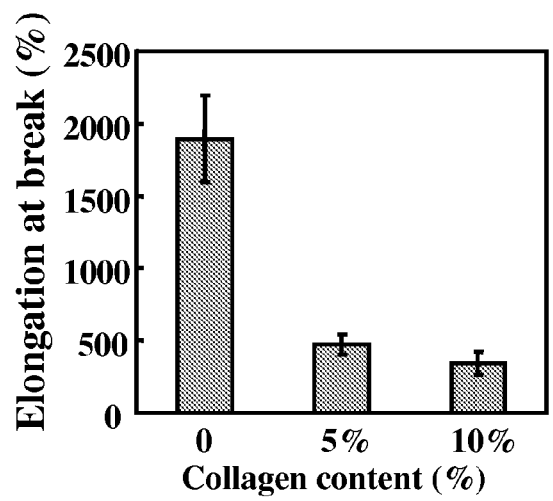
FIG. 12B is a graph quantifying the elongation at break at 37° C. of copolymers composed of NIPAAm/AAc/NHS/HEMAPLA (LA units) for various percentage content of collagen conjugating with the copolymer, showing that elongation at break decreases as the content of collagen increases.

FIG. 12A illustrates the effect of collagen incorporation on the tensile strength (measured in MPa) at 37° C. of P(NIPAAm-co-AAc-co-NHS-co-HEMAPLA) copolymers. The FIG. 12B shows the effect of the collagen on the elongation at break at 37° C. of P(NIPAAm-co-AAc-co-NHS-co-HEMAPLA) copolymers. Both tensile strength and elongation at break decreases as the content of collagen increases (p<0.05). The hydrogel is still flexible, with elongation at break greater than 340% and tensile strength greater than 0.3 MPa.

Figure 13A:
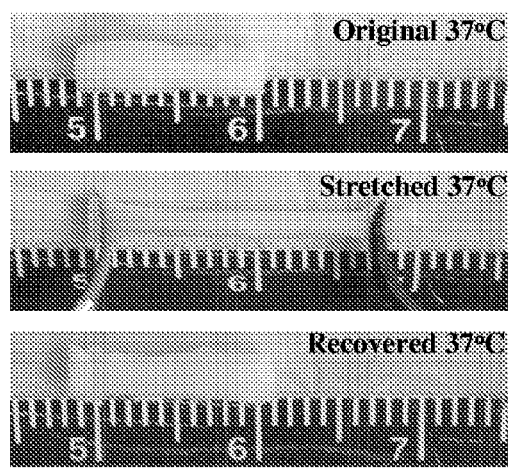
FIGS. 13A-13B are macroscopic photographs of the P(NIPAAm-co-AAc-co-NHS-co-HEMAPLA2.1)85/6/5/4 hydrogel in aqueous conditions at different temperatures and stretching conditions.
Figure 13B:
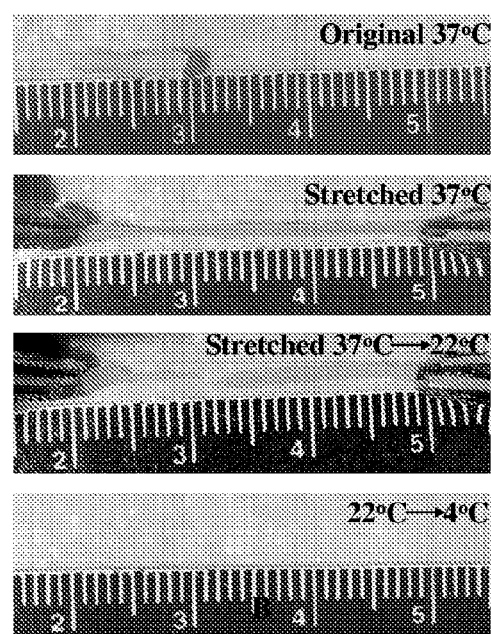

FIG. 13 shows macroscopic images of the morphological changes in the P(NIPAAm-co-AAc-co-NHS-co-HEMAPLA2.1) 85/6/5/4 copolymer after stretching and temperature change in an aqueous environment. In FIG. 13A, a strain of 100% was applied and was followed by a recovery period, where 91% strain recovery was observed. When the stretched hydrogel was cooled from 37° C. to 22° C., the material fractured. Upon further cooling to 4° C., hydrogel solubilized completely in water (FIG. 13B).

Figure 14:
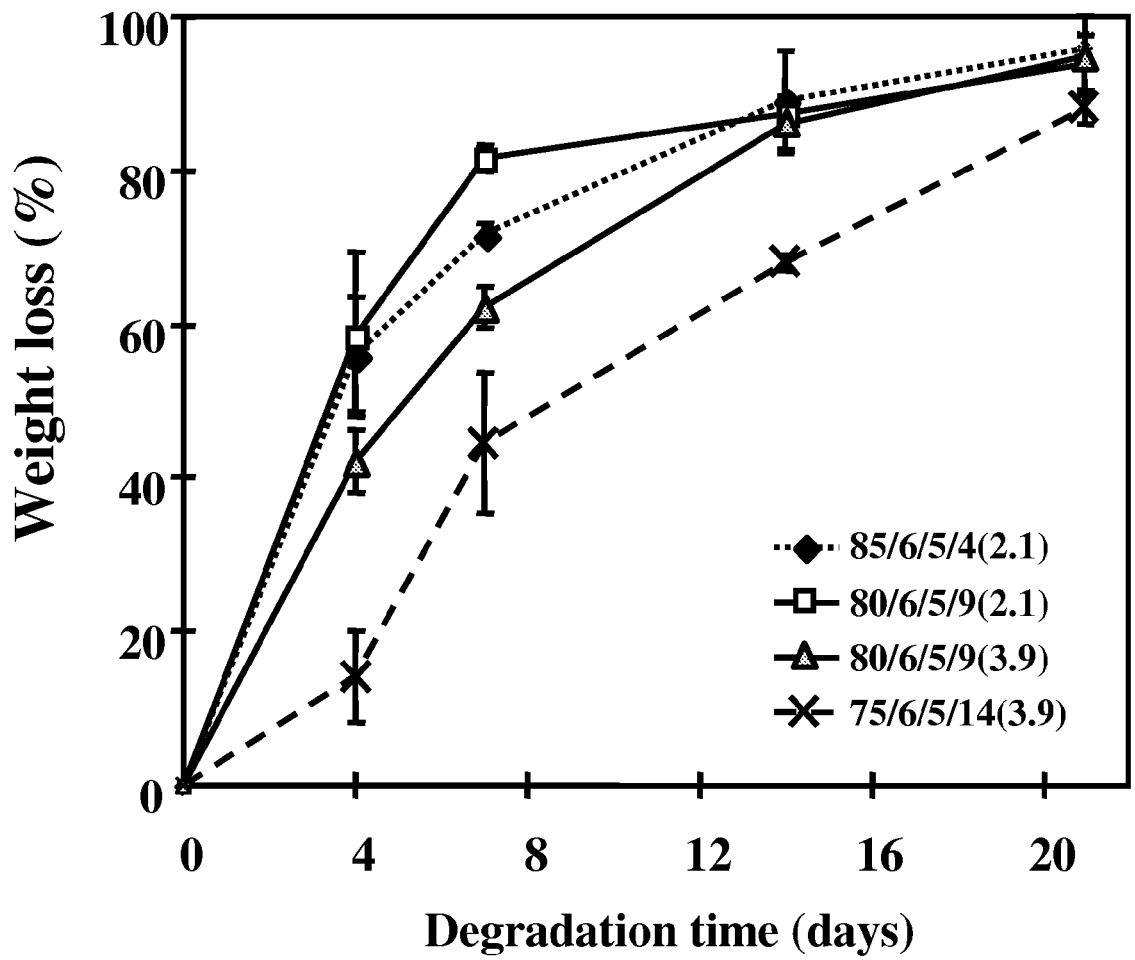
FIG. 14 is a graph showing the degradation at 37° C. in PBS of the copolymer composed of NIPAAm/AAc/NHS/HEMAPLA (LA units) in which weight loss of the copolymer for various feed ratios is quantified as a function of time.

FIG. 14 shows the effect of the feed ratio of the P(NIPAAm-co-AAc-co-NHS-co-HEMAPLA) copolymer on degradation at 37° C. in PBS, which was quantified by percentage weight loss. Weight loss was measured by mass change before and after degradation. For hydrogels with PLA lengths of 2.1, the decrease of NIPAAm/HEMAPLA ratio did not significantly affect weight loss during 21 days of degradation (p>0.05). However, when the PLA length was 3.9, a decrease in the NIPAAm/HEMAPLA ratio significantly decreased the mass lss during the degradation period (p<0.05). With the same NIPAAm/HEMAPLA ratio, an increase in the PLA length from 2.1 to 3.9 decreased mass loss in the first 7 days (p<0.05).

Figure 15:
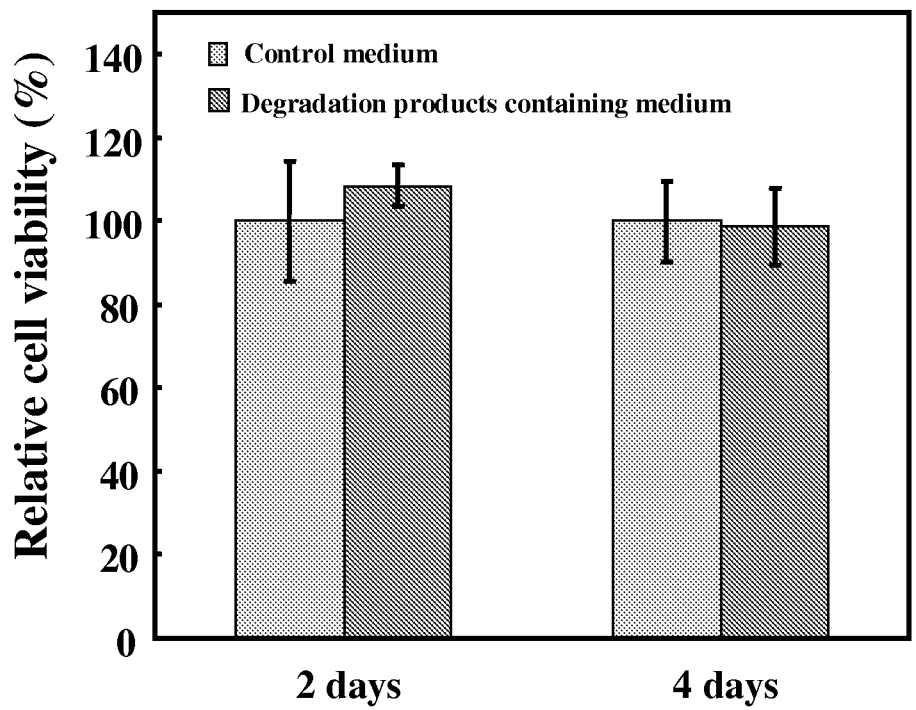
FIG. 15 is a graph showing the lack of cytotoxicity at 37° C. of the P(NIPAAm-co-AAc-co-NHS-co-HEMAPLA) copolymer, where the relative cell viability of smooth muscle cells (SMC) is quantified at 2 days and at 4 days for control medium and for medium with 1.7 mg/mL of degraded copolymer.

FIG. 15 illustrates the lack of cytotoxicity at 37° C. of the degraded P(NIPAAm-co-AAc-co-NHS-co-HEMAPLA) copolymer to smooth muscle cells (SMC). SMC were plated on control culture medium and on culture medium containing 1.7 mg/mL of degraded copolymer. After 48 h and 96 h after culturing the cells, relative cell viability of SMC was determined by a colormetric (MTT) assay to measure mitochondrial activity of the cells. With the unsupplemented medium resulting in a cell density defined as 100% at each time point, the culture medium containing the degraded copolymer resulted in cell densities of 109±5% after day 2 and of 99±9% after day 4. The cell densities were not significantly different between control and degraded polymer-containing medium at both time points (p>0.05).

Figure 16:
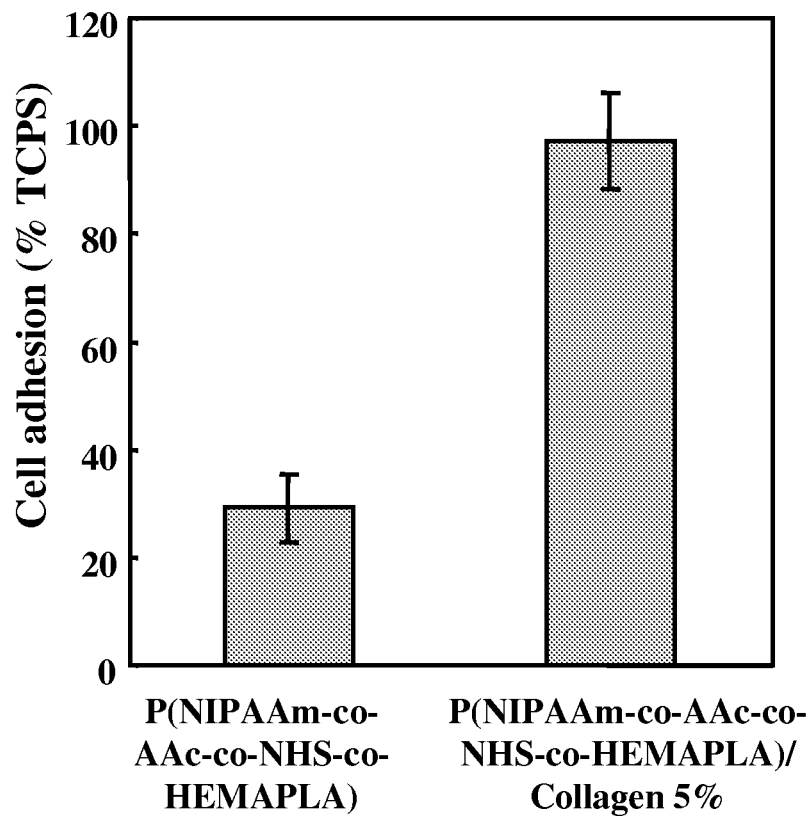
FIG. 16 is a graph showing the viability of SMC on the surface of the P(NIPAAm-co-AAc-co-NHS-co-HEMAPLA) copolymer, where cell adhesion relative to the tissue culture plate (% TCPS) increases with the conjugation of collagen to the copolymer.

The viability of SMC on the surface of the P(NIPAAm-co-AAc-co-NHS-co-HEMAPLA) copolymer is shown in FIG. 16. Smooth muscle cells were cultured on the surface of copolymer hydrogel with or without collagen. SMCs were seeded at a density of $3 \times 10^5$/mL and cultured for 24 h. The hydrogel without collagen showed 29% (p<0.01) cell adhesion as compare to tissue culture plate (TCPS); the collagen containing hydrogel significantly improved cell adhesion to 97% (p<0.01 versus 0% collagen). Cell adhesion was measured by MTT.

To evaluate cell viability after encapsulation within the hydrogel matrices, SMCs were first labeled with living cell marker CellTracker Green CMFDA (5-chloromethylfluorescein diacetate in DMSO, Invitrogen of Carlsbad, Calif.) by exposing a cell suspension to culture media containing 10 µM of CMFDA. The cell suspension was incubated for 37° C. for 15 min, followed by centrifugation. The cell pellet was resuspended in culture medium and washed twice to remove free CMFDA. A 20% of P(NIPAAm-co-AAc-co-NHS-co-HEMAPLA3.9) PBS solution with or without 5% collagen was pre-cooled to 4° C. A labeled cell suspension (0.25 mL of $2 \times 10^7$ cells/mL of PBS) was mixed thoroughly with 1 mL of copolymer solution. The mixture was transferred into a 37° C. water bath for gelation for 10 min. The water expelled from the hydrogel was removed and replaced with an equal volume of medium comprising PBS and 20% fetal bovine serum. The medium was changed daily for 7 days. The hydrogel was cut into ~100 µm thick pieces and visualized with fluorescence microscopy.

Figure 17:
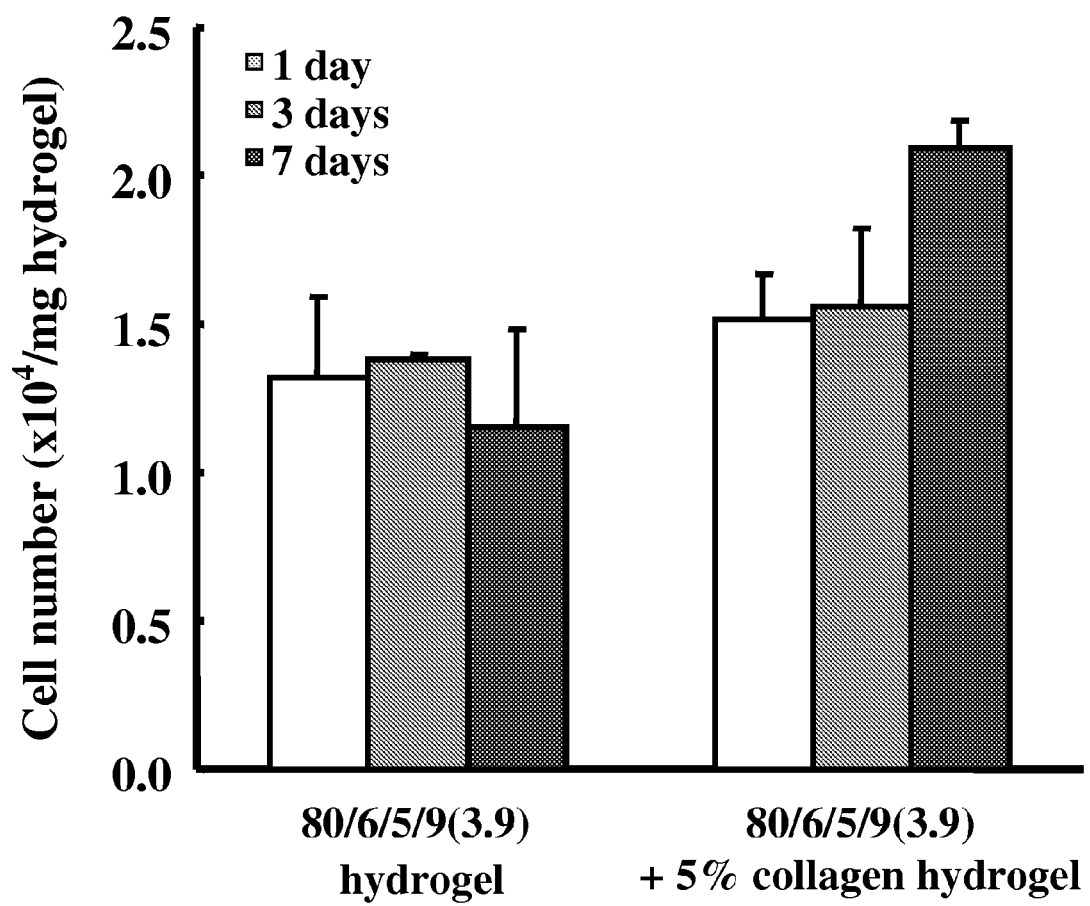
FIG. 17 is a graph showing the cell density for SMCs encapsulated within P(NIPAAm-co-AAc-co-NHS-co-HEMAPLA) copolymer, either without (0%) or with 5% collagen, over a period of seven days.
Figure 18A:
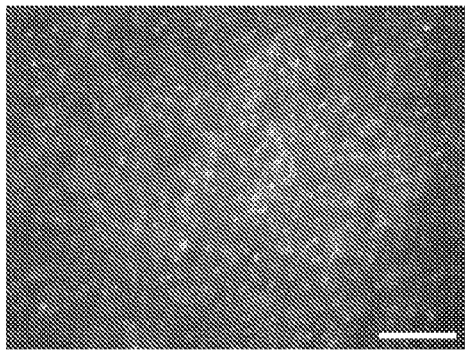
FIGS. 18A-18F are fluorescence photomicrographs of SMCs encapsulated within P(NIPAAm-co-AAc-co-NHS-co-HEMAPLA) copolymer. SMC encapsulation within hydrogels is shown for copolymer without collagen (FIGS. 18A, 18C, and 18E) and with collagen (FIGS. 18B, 18D, and 18F). Cells were cultured in hydrogels for 0 (A and B), 3 (C and D) or 7 days (E and F). Scale bar=200 μm.
Figure 18B:
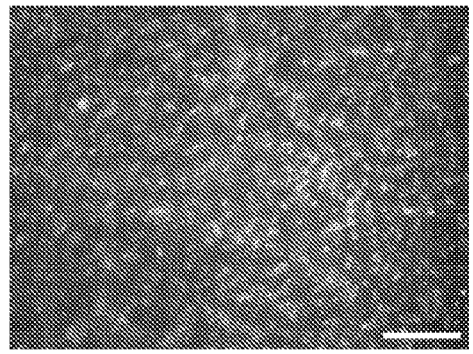
Figure 18C:
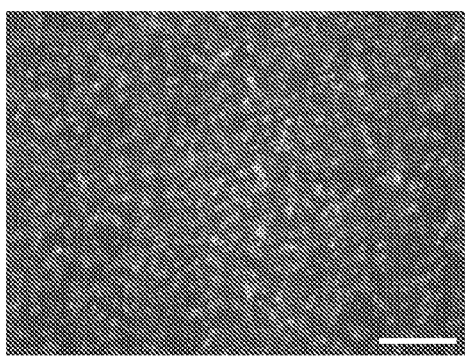
Figure 18D:
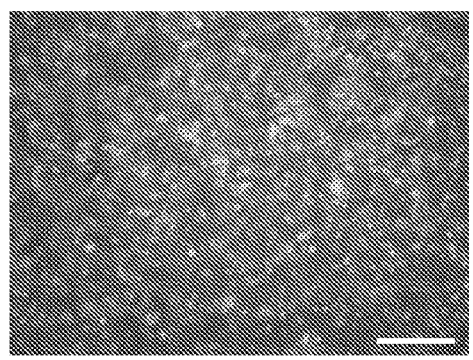
Figure 18E:
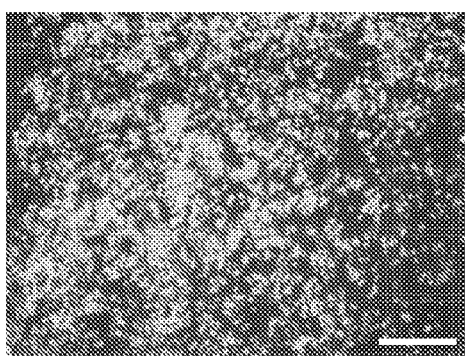
Figure 18F:
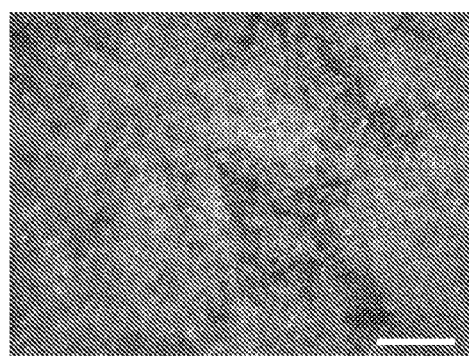

FIG. 17 shows the cell density of encapsulated SMCs over a period of 7 days. Hydrogels containing 0% and 5% collagen had encapsulation efficiency of 92±4% and 95±2%, respectively. Cell-encapsulated hydrogels without collagen had a tensile strength of 0.66±0.10 MPa and elongation at break of 1600±135%, while cell-encapsulated hydrogels with 5% collagen had a tensile strength of 0.44±0.04 MPa and elongation at break of 850±±81%. Cell density was high for both hydrogels after encapsulation (FIGS. 18A and 18B). Cells remained alive during 7 days culture. Cell density did not change obviously after 3 days (FIGS. 18C and 18D). After 7 days, collagen containing hydrogel exhibited higher cell density than non-collagen containing hydrogel (FIGS. 18E and 18F).

Data are expressed as mean±standard deviation. Statistical analysis was performed by ANOVA with post hoc Neuman-Keuls testing for differences. For hydrogel dehydration data, hydrogels with different lactate length and PNIPAAm/HEMAPLA ratio were compared with repeated measures ANOVA to evaluate the effect on weight loss.

Example 2

Flexible, Injectable and Thermosensitive Poly(NIPAAm-co-NHS) Hydrogel

This copolymer is similar to the copolymer of Example 1, but possessing a different degradation mechanism due to its lack of ester linkages in the backbone. The polymer is a copolymer of N-isopropylacrylamide and acrylic N-hydroxysuccinimide ester. The N-isopropylacrylamide serves as the thermosensitive component after polymerization and the acrylic N-hydroxysuccinimide ester is for conjugation of biomolecules. A copolymer of N-isopropylacrylamide and acrylic acid is used as control. This copolymer is synthesized by BOP-initiated radical polymerization substantially as described in Example 1. Table 4 provides monomer feed ratios and composition of the resultant copolymer as determined by $^1$H-NMR.

TABLE 4

Synthesis of Poly(NIPAAm-co-NHS-co-AAc)

| Polymer | Feed ratio (NIPAAm/NHS/AAc) | Composition (NIPAAm/NHS/AAc)* |
| --- | --- | --- |
| P(NIPAAm-co-NHS-co-AAc) = 90/0/10 | 90:0:10 | 90.2:0:9.8 |
| P(NIPAAm-co-NHS-co-AAc) = 90/10/0 | 90.0:10.0:0 | 88.7:11.3:0 |
| P(NIPAAm-co-NHS-co-AAc) = 93.5/0/6.5 | 93.5:0:6.5 | 92.7:0:7.3 |
| P(NIPAAm-co-NHS-co-AAc) = 93.5/6.5/0 | 93.5:6.5:0 | 92.1:7.9:0 |
| P(NIPAAm-co-NHS-co-AAc) = 80/20/0 | 80.0:20.0:0 | 80.3:19.7:0 |

*Determined by 1H-NMR

Conjugation of the thermosensitive polymer with collagen: The thermosensitive polymer dissolved in PBS (pH=7.4) to 20 wt %. Type I collagen solution (4 wt %) was mixed with the thermosensitive polymer solution at 4° C. The final collagen content was 5% and 10%. The mixture was set at 4° C. overnight to react the NHS residues and collagen.

Figure 19:
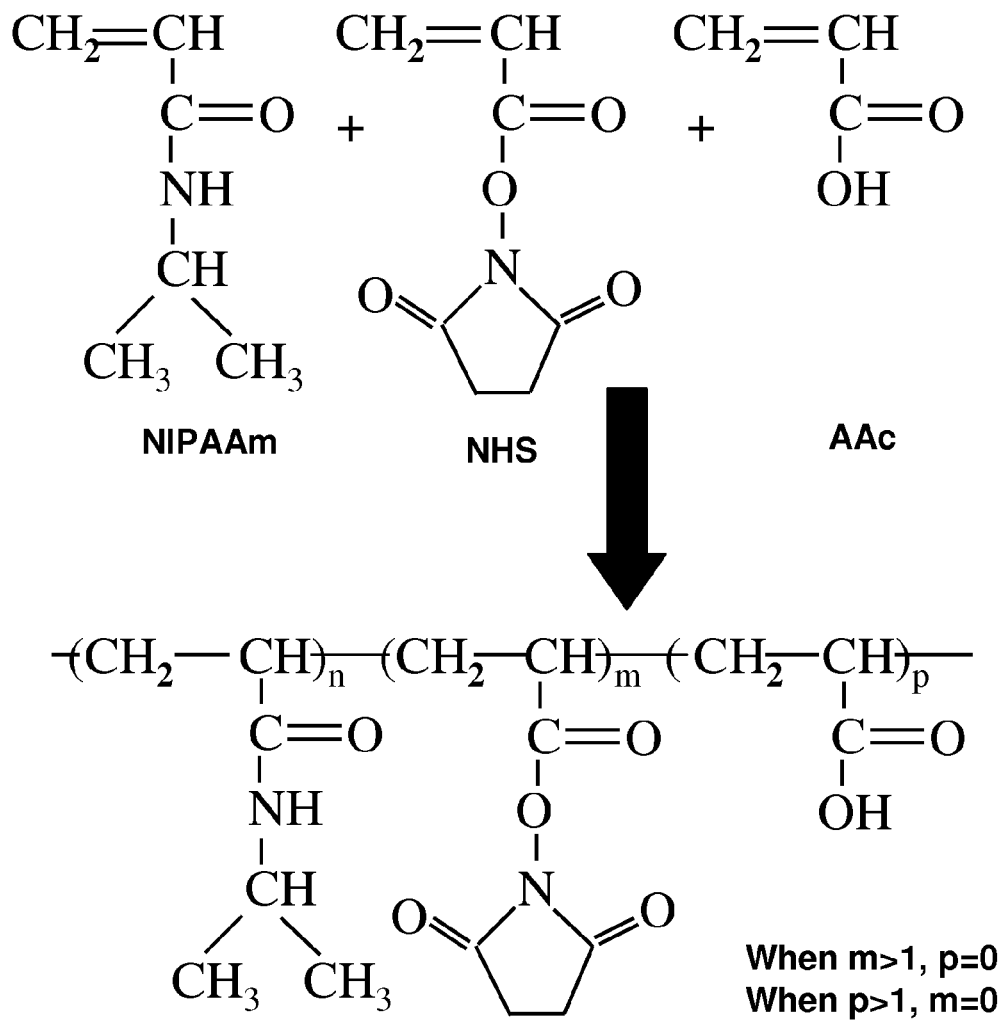
FIG. 19 is a schematic drawing for the synthesis of copolymer composed of N-isopropylacrylamide (NIPAAm), acrylic N-hydroxysuccinimide ester (NHS), and acrylic acid (AAc).
Figure 20A:
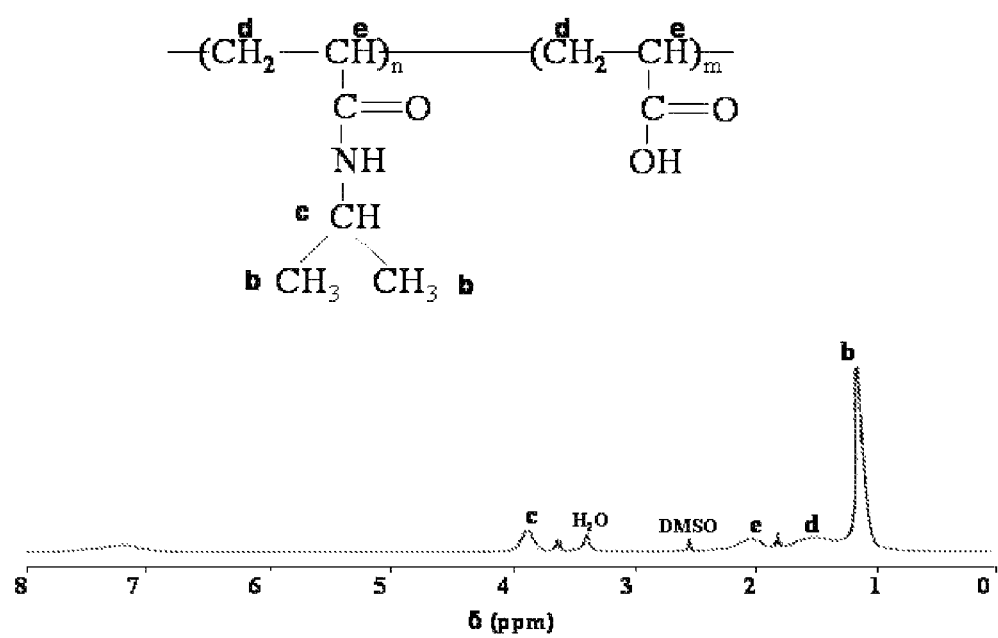
FIG. 20A is a 1H-NMR spectrum of the P(NIPAAm-co-AAc) copolymer composed of N-isopropylacrylamide (NIPAAm), and acrylic acid (AAc), where characteristic peaks of protons are labeled from a to e according to the structure shown.
Figure 20B:
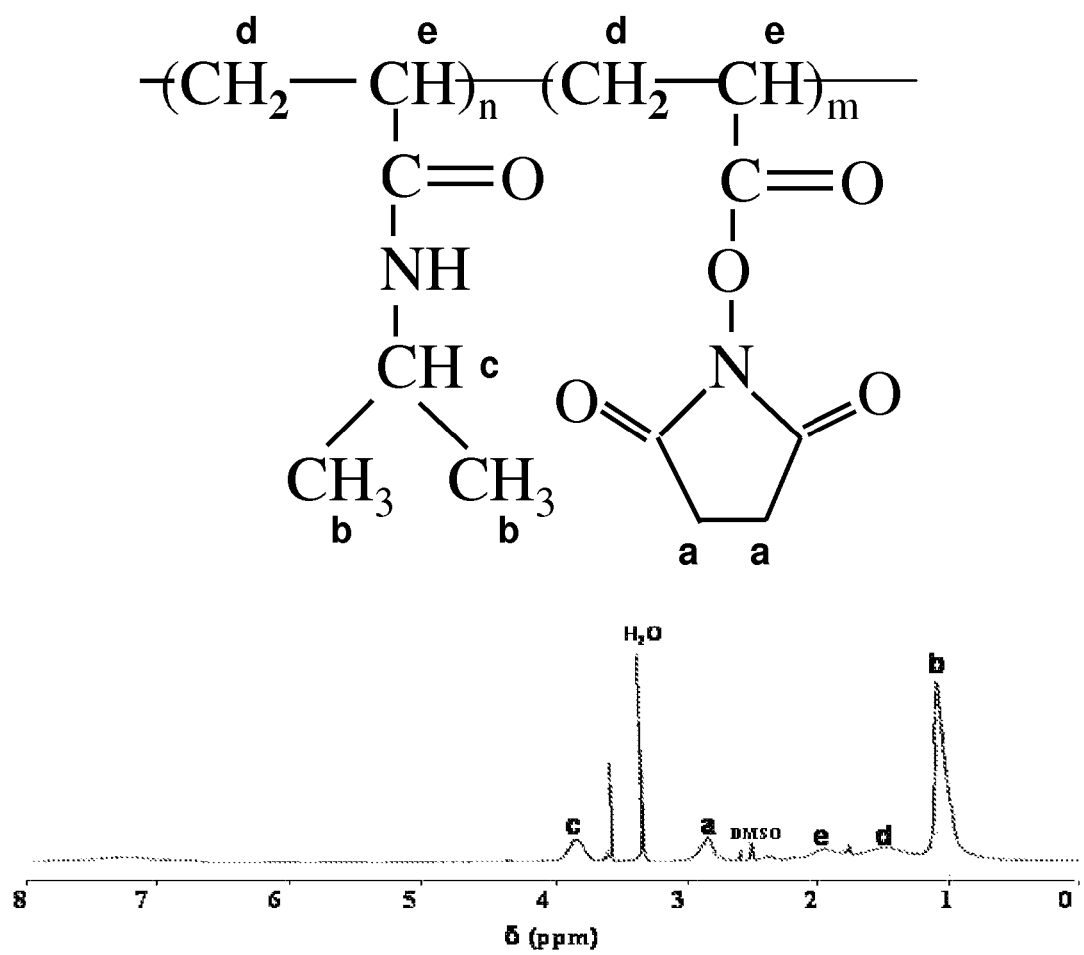
FIG. 20B is a 1H-NMR spectrum of the P(NIPAAm-co-NHS) copolymer composed of N-isopropylacrylamide (NIPAAm), and acrylic N-hydroxysuccinimide ester (NHS), where characteristic peaks of protons are labeled from a to e according to the structure shown.

FIG. 19 illustrates the synthesis of P(NIPAAm-co-NHS) copolymer and of P(NIPAAm-co-AAc) copolymer. FIG. 20A shows the $^1$H-NMR spectrum for the control, P(NIPAAm-co-AAc) copolymer. FIG. 20B shows the $^1$H-NMR spectrum for P(NIPAAm-co-NHS) copolymer. A peak from the proton on the NHS unit is shown on the spectra at ~2.8 ppm (labeled a).

Figure 21:
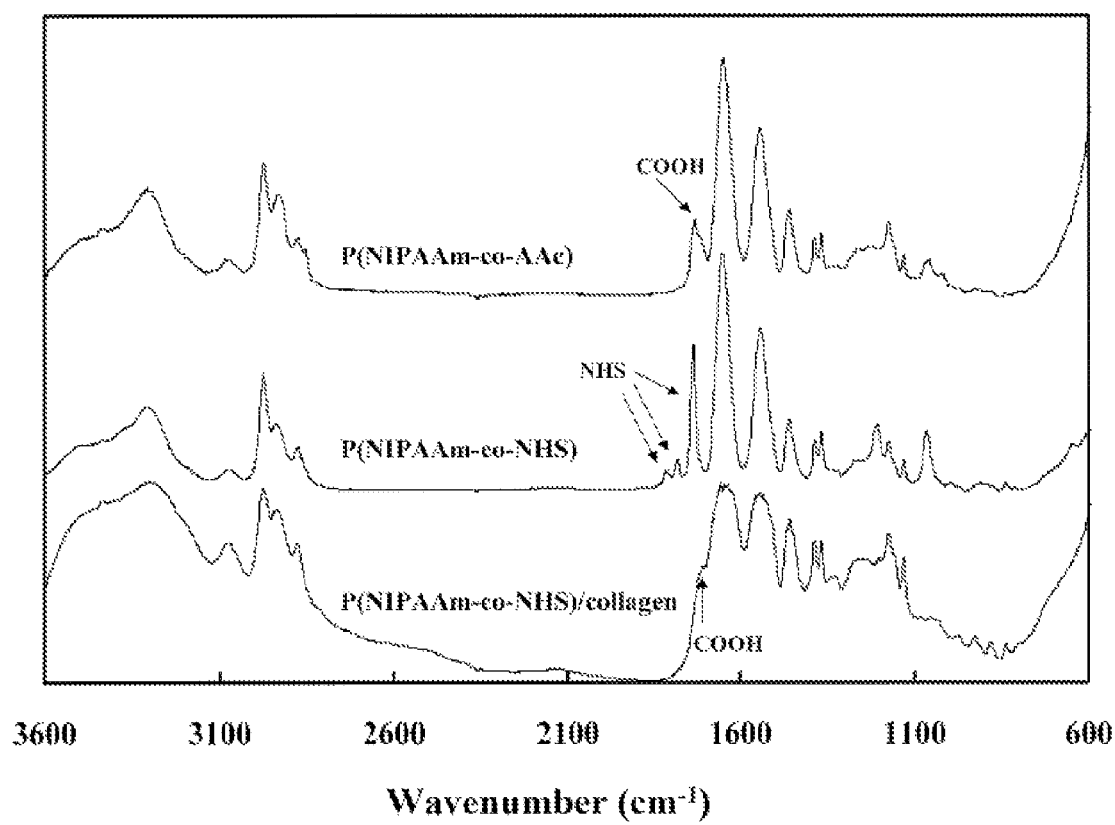
FIG. 21 is a FT-IR spectrum of the P(NIPAAm-co-AAc) copolymer, P(NIPAAm-co-NHS) copolymer, and P(NIPAAm-co-NHS) copolymer conjugated with collagen.

FIG. 21 shows the absorptions of the P(NIPAAm-co-NHS) copolymer with and without collagen and of the P(NIPAAm-co-AAc) copolymer. The FT-IR spectrum labeled "P(NIPAAm-co-NHS)/collagen" does not show absorption of NHS groups, indicating complete reaction between the P(NIPAAm-co-NHS) copolymer and collagen. The small COOH group absorption peak is probably from NHS hydrolysis. The amide absorption peak at 1650 cm$^{-1}$ was enhanced in comparison with FT-IR spectra for P(NIPAAm-co-NHS) and for P(NIPAAm-co-AAc).

Figure 22:
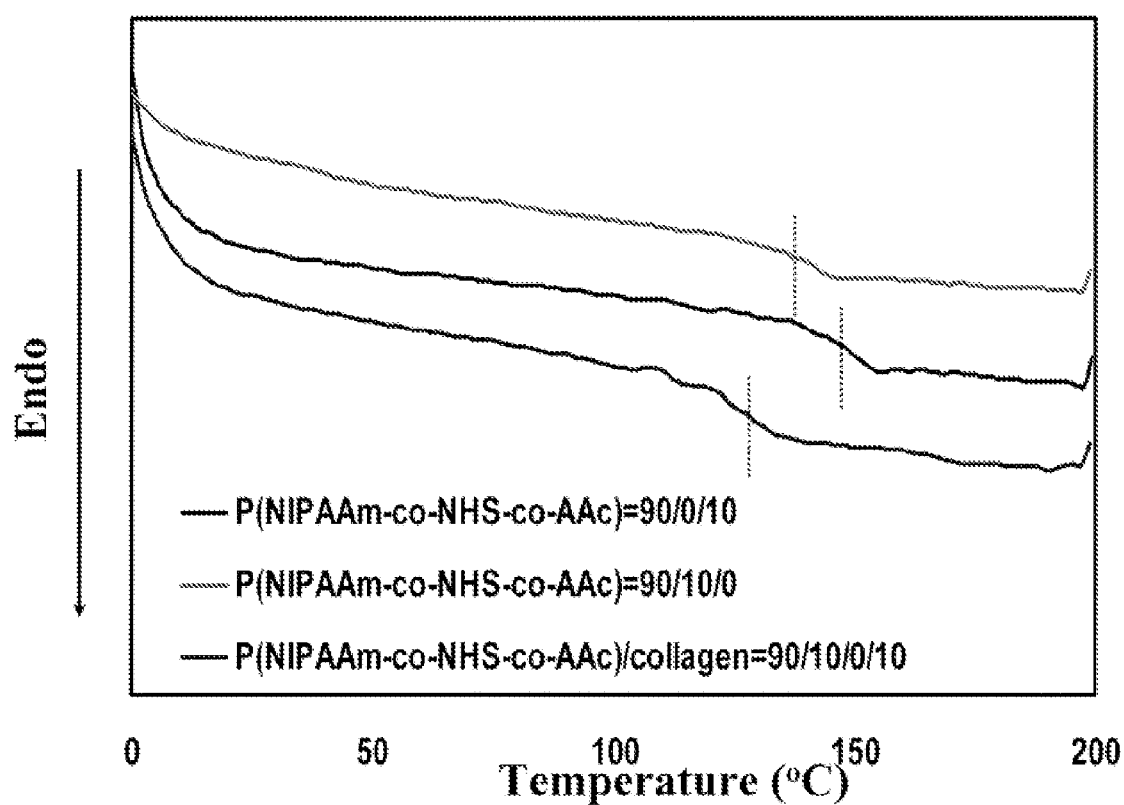
FIG. 22 is a thermal analysis by differential scanning calorimetry of the P(NIPAAm-co-AAc) copolymer, P(NIPAAm-co-NHS) copolymer, and P(NIPAAm-co-NHS) copolymer conjugated with collagen, where glass transition temperature of P(NIPAAm-co-NHS) or P(NIPAAm-co-NHS) conjugated with collagen is lower than the glass transition temperature of P(NIPAAm-co-AAc).

FIG. 22 shows the glass transition temperature of the P(NIPAAm-co-AAc) copolymer, and P(NIPAAm-co-NHS) copolymer with and without collagen. Thermal analysis was determined by differential scanning calorimetry. The glass transition temperature of P(NIPAAm-co-NHS) copolymer is lower with collagen, indicating a strong interaction between the copolymer and collagen.

Figure 23:
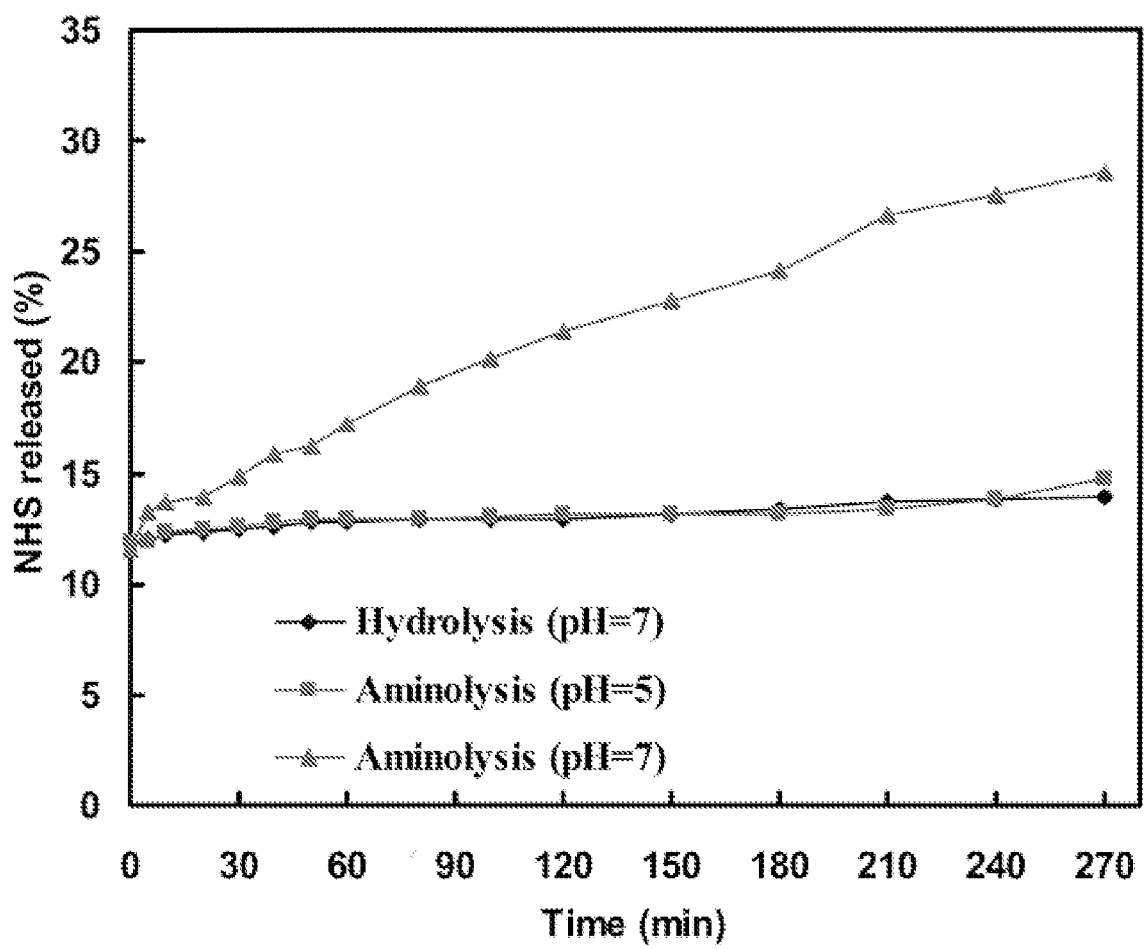
FIG. 23 is a graph showing bioconjugating kinetics at 4° C. measured by UV-Vis at 260 nm, where the release of NHS from a P(NIPAAm-co-NHS) copolymer is measured as a function of time under conditions for hydrolysis at pH of 7 and for aminolysis by glycine at pH of 5 and of 7.

FIG. 23 shows the kinetics of bioconjugation at 4° C. for the P(NIPAAm-co-NHS) 90/10 copolymer. The release of NHS was measured by UV-Vis at 260 nm. Kinetics was measured with 0.3 mg/mL of copolymer, where aminolysis conditions were with 0.5 mg/mL of glycine. The reaction between the NHS unit in copolymer and glycine is gradual at pH=7, and the aminolysis reaction is very slow at pH=5. Hydrolysis of NHS unit in copolymer is very slow at pH=7.

Figure 24:
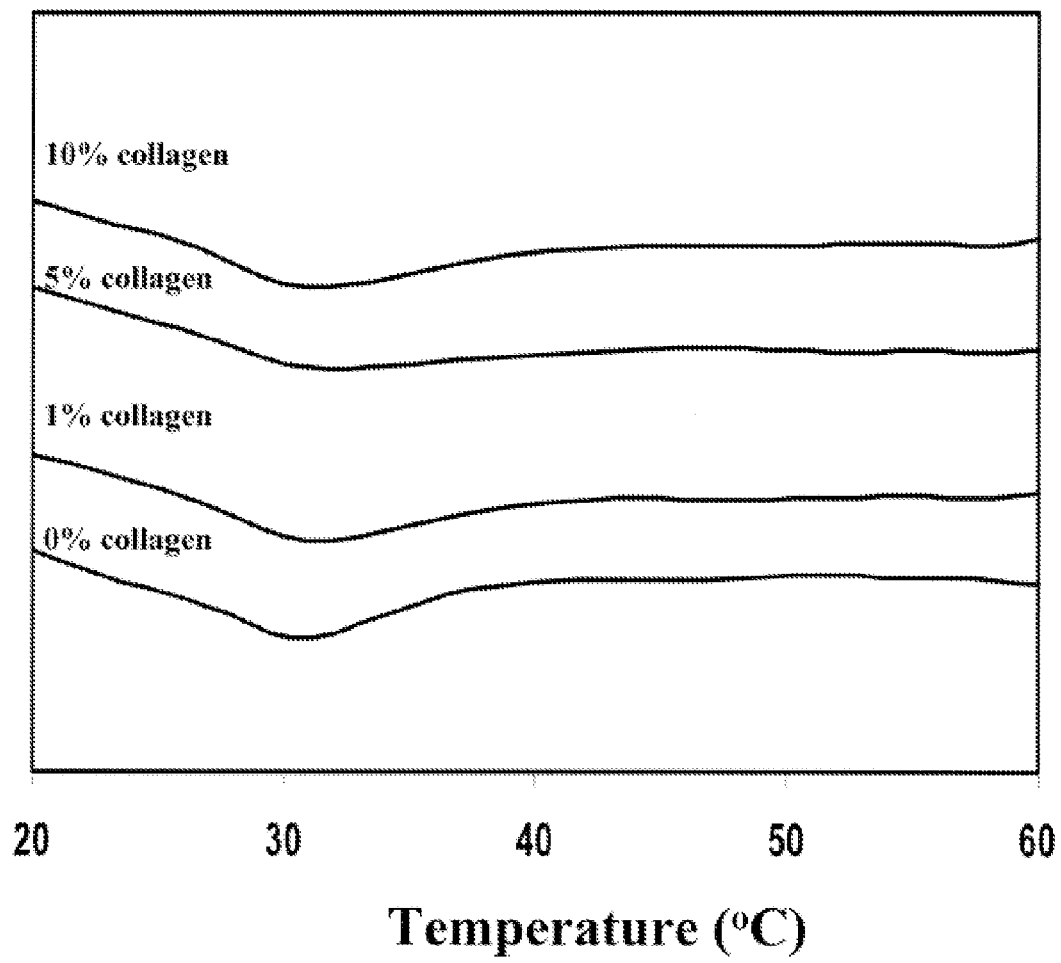
FIG. 24 is a graph showing the effect of the conjugation of collagen on the lower critical solution temperature (LCST) of a P(NIPAAm-co-NHS) copolymer in a feed ratio of 90/10, where the LCST is measured by Differential Scanning Calorimetry (DSC).
Figure 25:
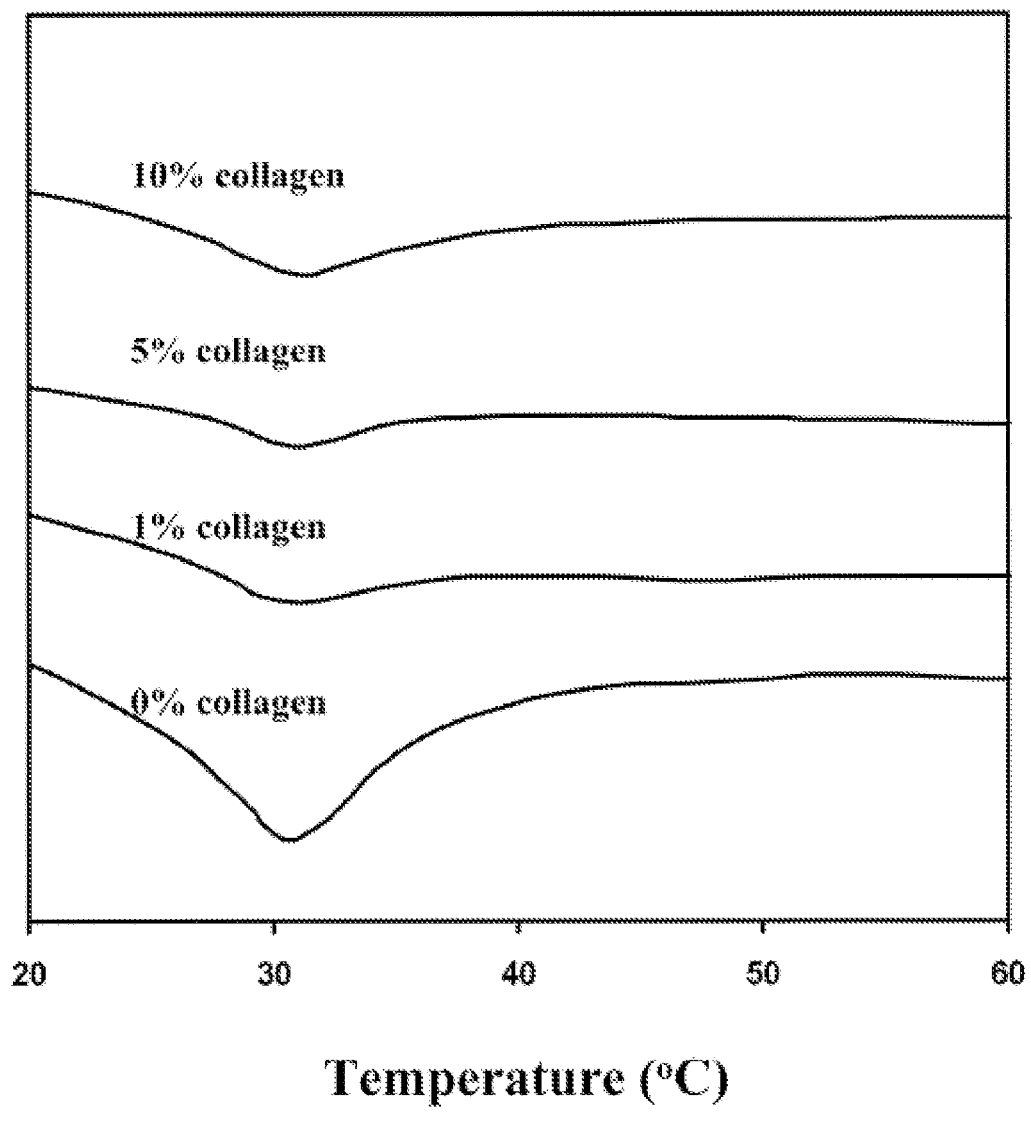
FIG. 25 is a graph showing the effect of the conjugation of collagen on the lower critical solution temperature (LCST) of a P(NIPAAm-co-NHS) copolymer in a feed ratio of 93.5/6.5, where the LCST is measured by Differential Scanning Calorimetry (DSC).
Figure 26:
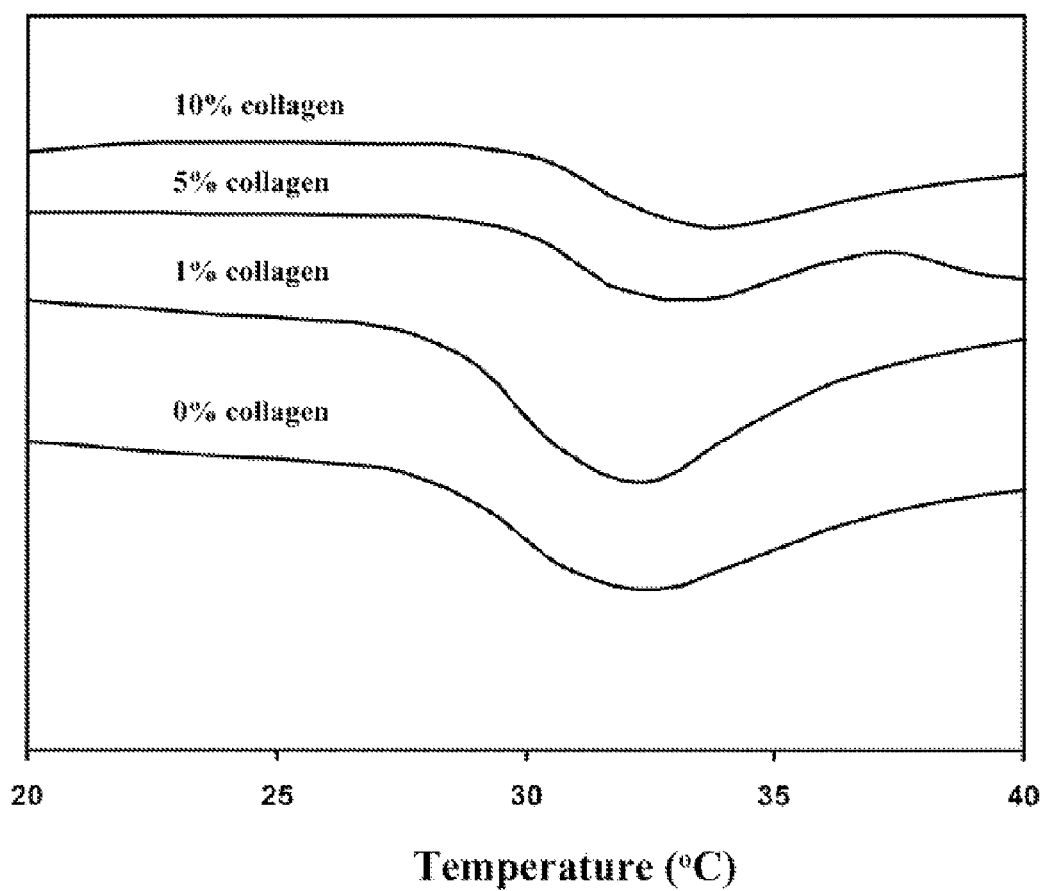
FIG. 26 is a graph showing the effect of the conjugation of collagen on the lower critical solution temperature (LCST) of a P(NIPAAm-co-AAc) copolymer in a feed ratio of 93.5/6.5, where the LCST is measured by Differential Scanning Calorimetry (DSC).

FIG. 24 illustrates the effect of the conjugation of collagen on the lower critical solution temperature (LCST) of P(NIPAAm-co-NHS) 90/10 copolymer. LCST was determined by Differential Scanning Calorimetry (DSC), inflection point. The LCST is seen to increase as the content of collagen is increased. The effect of the conjugation of collagen on the lower critical solution temperature (LCST) of P(NIPAAm-co-NHS) 93.5/6.5 copolymer is illustrated in FIG. 25, where LCST is seen to increase as the content of collagen increases. FIG. 26 shows the effect of conjugation of collagen on the lower critical solution temperature (LCST) of P(NIPAAm-co-AAc) 93.5/6.5 copolymer, where LCST is seen to increase as the content of collagen increases.

Figure 27:
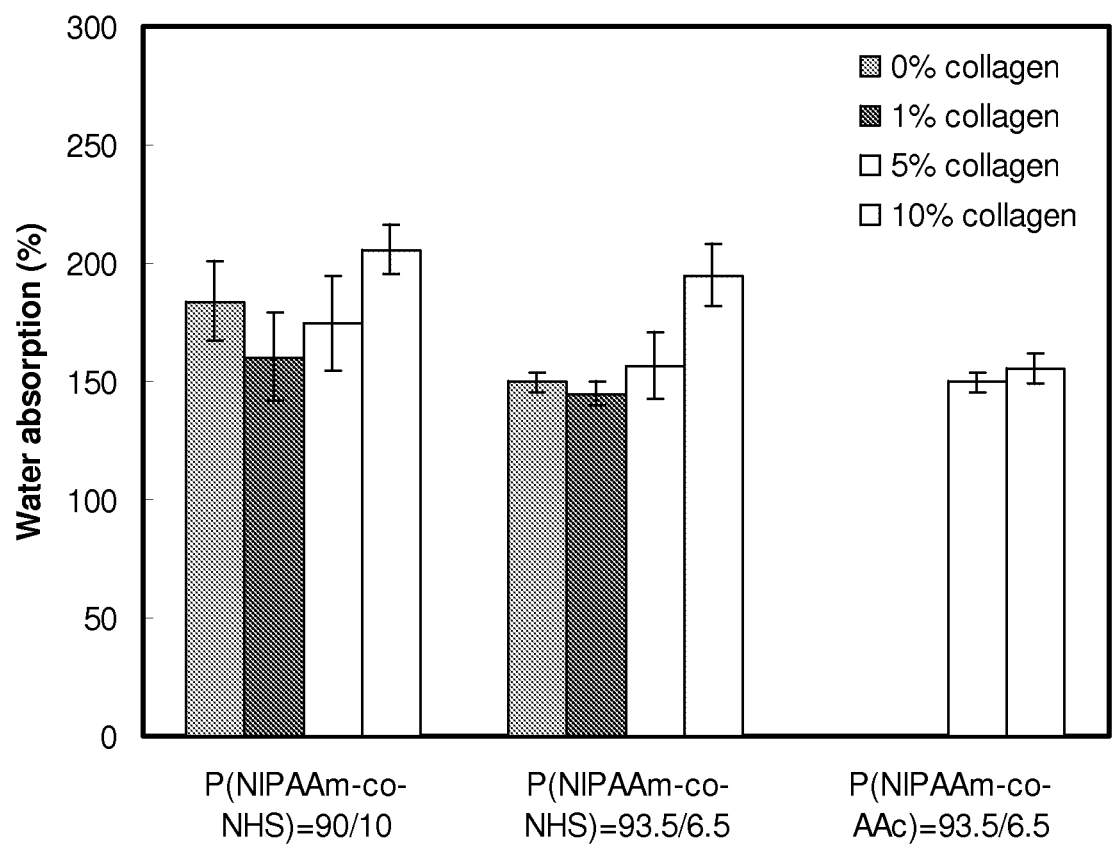
FIG. 27 is a graph showing the effect of the conjugation of collagen on the rate of water absorption at 37° C. of P(NIPAAm-co-AAc) copolymer or of P(NIPAAm-co-NHS) copolymer for two feed ratios, illustrating that the highest content of collagen results in the highest water absorption.

FIG. 27 shows the effect of the conjugation of collagen on the rate of water absorption at 37° C. of P(NIPAAm-co-NHS) 90/10 copolymer, P(NIPAAm-co-NHS) 93.5/6.5 copolymer and P(NIPAAm-co-AAc) 93.5/6.5 copolymer. The copolymer conjugated with collagen has water absorption rate higher than 150%. The increase of the content of collagen to 5% did not change water absorption significantly. Copolymers with content of 10% collagen have the highest water absorption.

Figure 28:
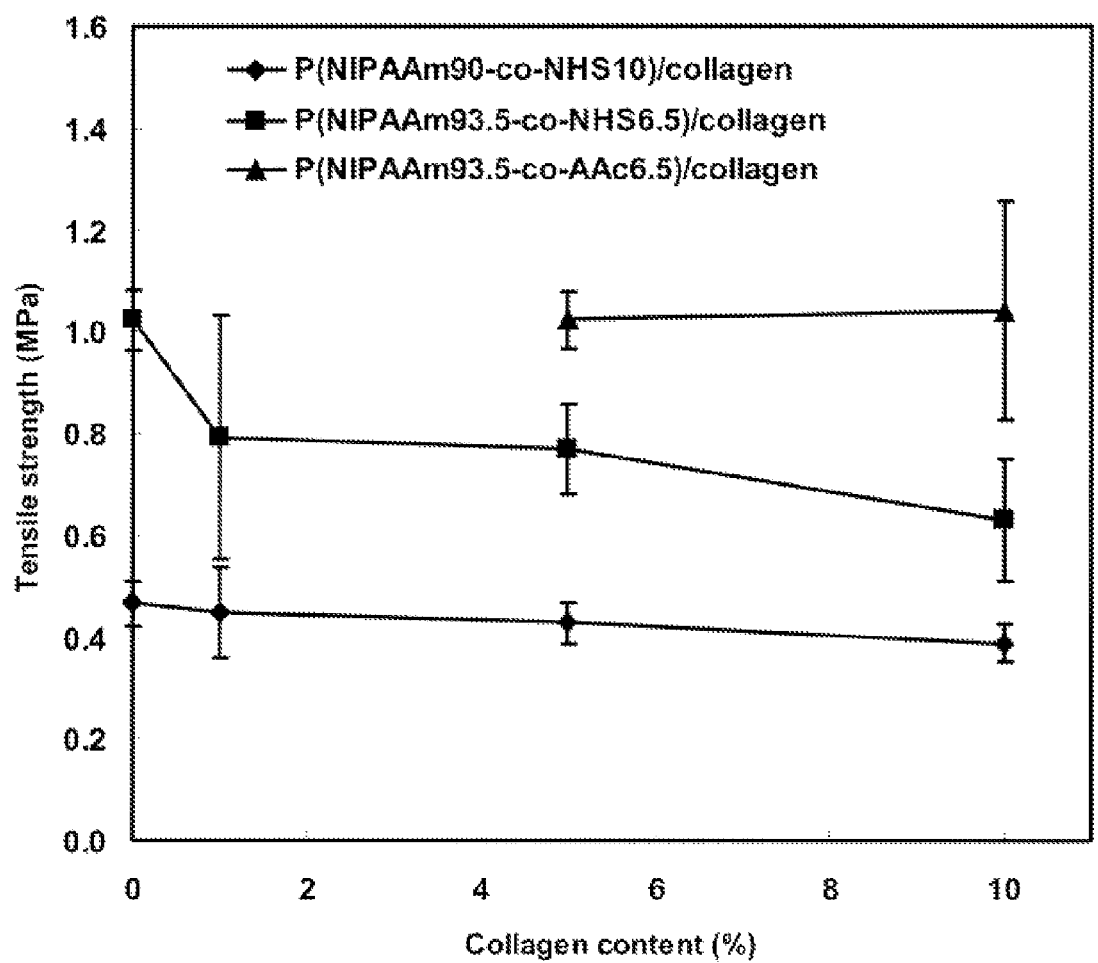
FIG. 28 is a graph showing the effect of the conjugation of collagen on the tensile strength of P(NIPAAm-co-AAc) copolymer or of P(NIPAAm-co-NHS) copolymer for two feed ratios, showing that tensile strength decreases as the content of collagen increases.

FIG. 28 illustrates the effect of the conjugation of collagen on the tensile strength of P(NIPAAm-co-NHS) 90/10 copolymer, P(NIPAAm-co-NHS) 93.5/6.5 copolymer and P(NIPAAm-co-AAc) 93.5/6.5 copolymer. The copolymers are relatively strong with tensile stress higher than 0.4 MPa. Tensile strength decreases as the content of collagen increases.

Figure 29:
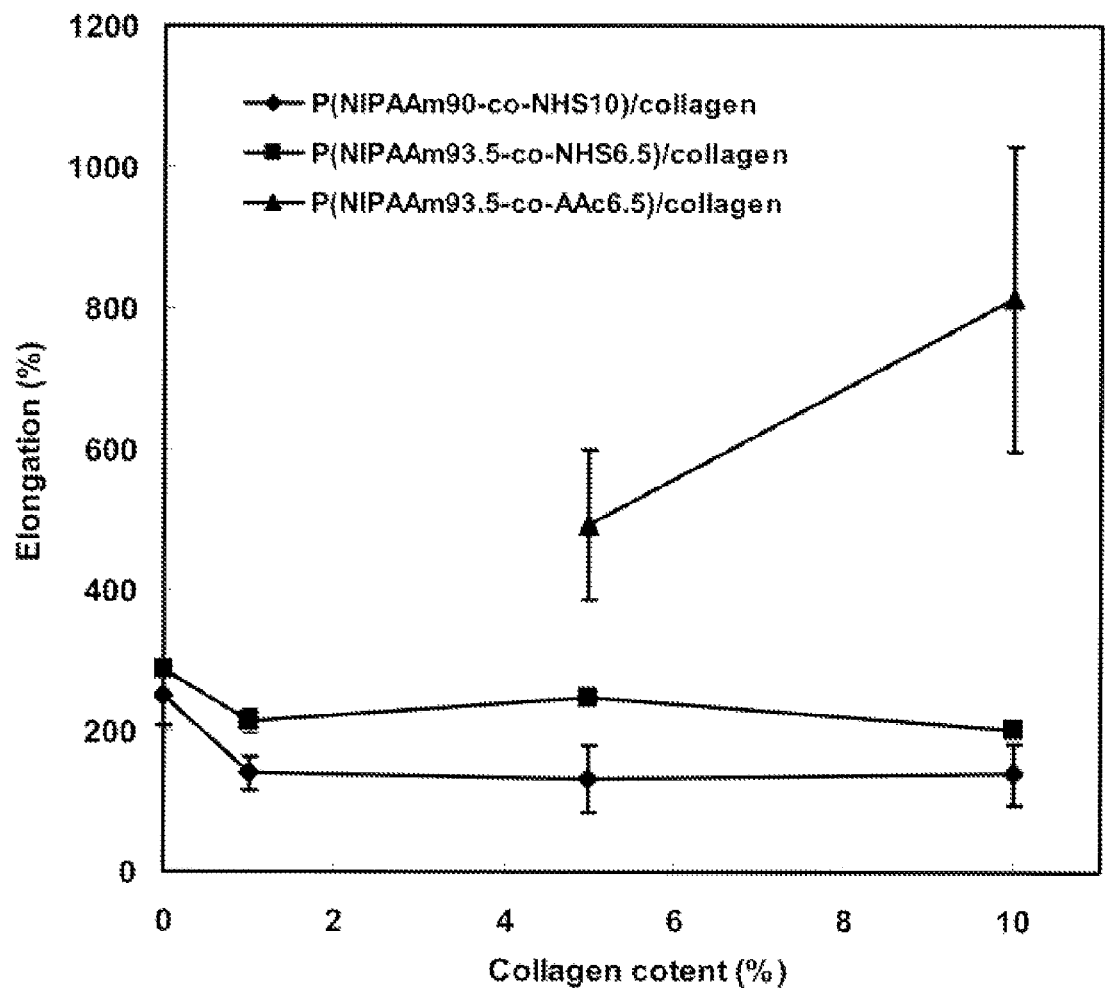
FIG. 29 is a graph showing the effect of the conjugation of collagen on the elongation at break of P(NIPAAm-co-AAc) copolymer or of P(NIPAAm-co-NHS) copolymer for two feed ratios, showing that elongation at break for P(NIPAAm-co-NHS) copolymer decreases as the content of collagen increases but the elongation at break for P(NIPAAm-co-AAc) copolymer increases as the content of collagen increases

FIG. 29 shows the effect of the conjugation of collagen on the elongation at break of P(NIPAAm-co-NHS) 90/10 copolymer, P(NIPAAm-co-NHS) 93.5/6.5 copolymer and P(NIPAAm-co-AAc) 93.5/6.5 copolymer. The hydrogel has elongation at break higher than 130%. Addition of collagen decreases the elongation at break slightly for copolymers with NHS groups. In contrast, the elongation at break increases with collagen content for copolymer without NHS groups.

Figure 30:
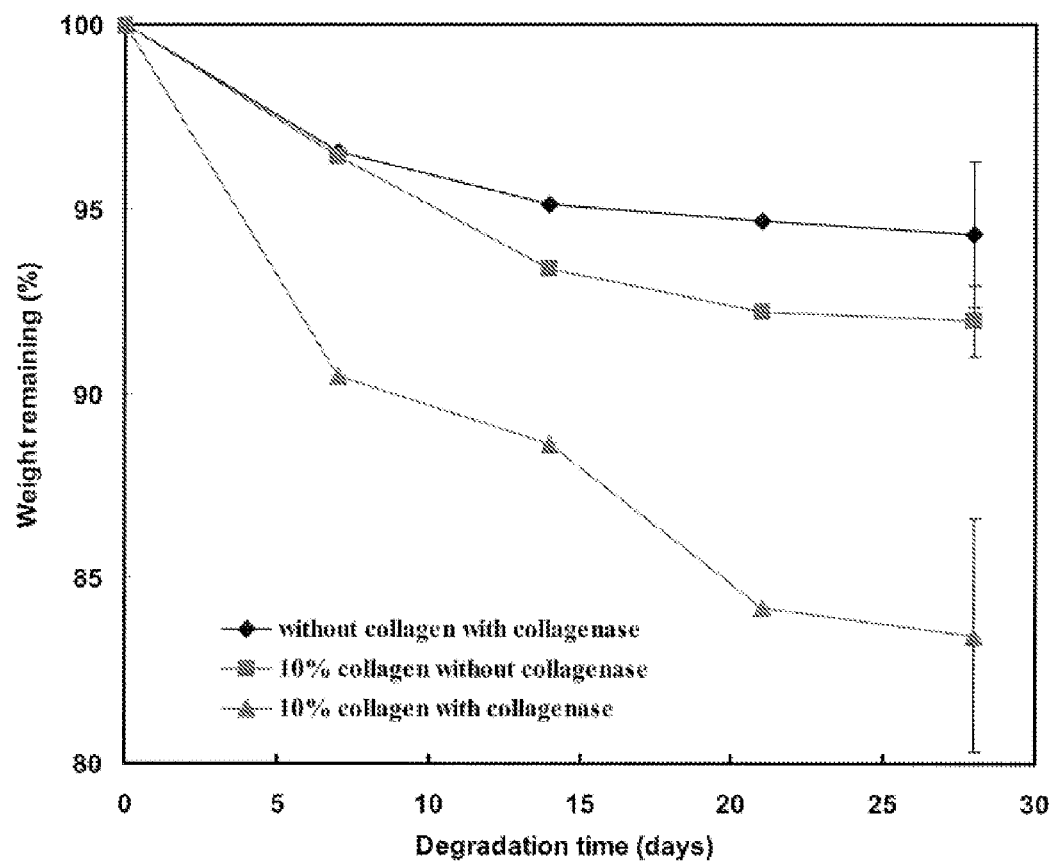
FIG. 30 is a graph showing the collagenase degradation of the copolymer poly(NIPAAm-co-NHS) collagen bioconjugates.

FIG. 30 shows the degradation of copolymer P(NIPAAm-co-NHS) 93.5/6/5 with and without collagen. Collagenase is used to cleave collagen. Copolymers containing collagen degrade faster than copolymers without collagen. The copolymer containing collagen degrades faster in the presence of collagenase than in the absence of collagenase.

Figure 31:
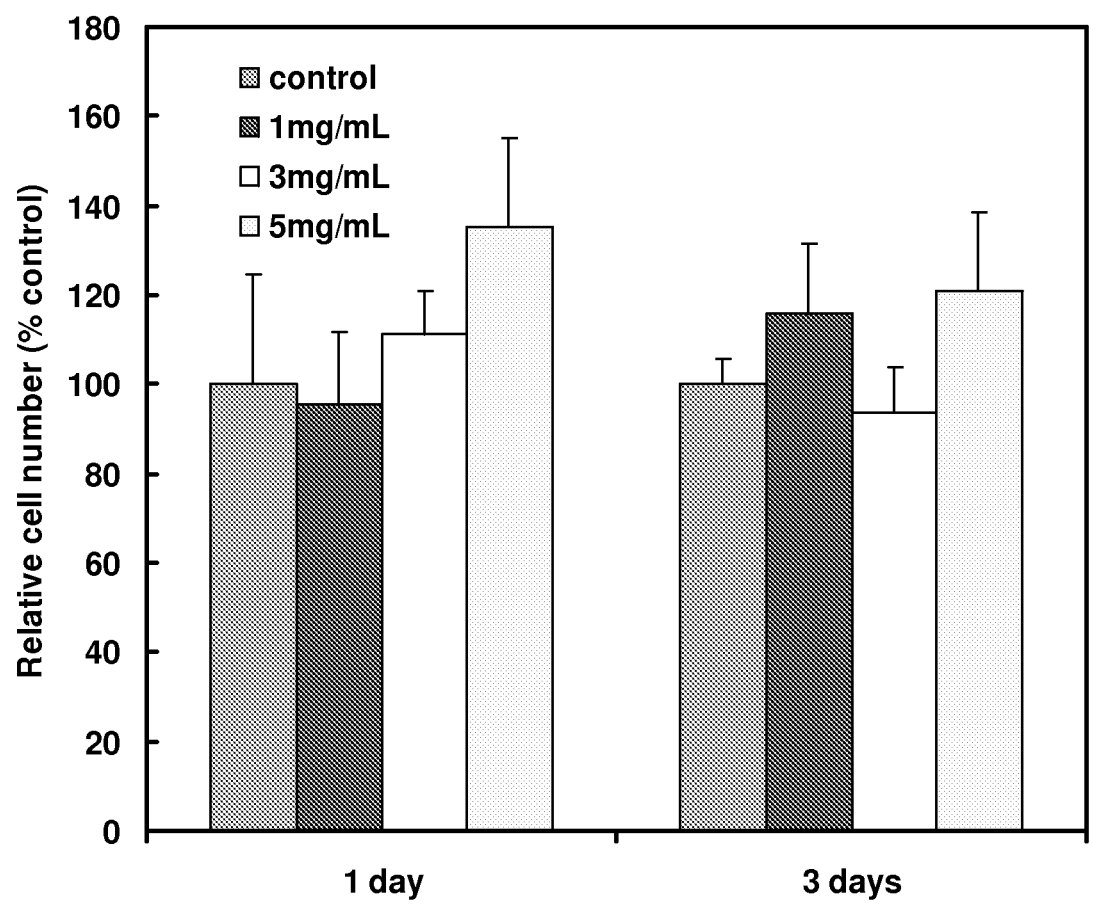
FIG. 31 is a graph showing the lack of cytotoxicity of P(NIPAAm-co-AAc) copolymer in a feed ratio of 90/10, in which MTT (3-(4,5-dimethylthiazolyl-2)-2,5-diphenyltetrazolium bromide) assay was used to measure the relative cell viability of smooth muscle cells (SMC) on tissue culture plate supplemented with medium containing various concentration of the copolymer.

FIG. 31 illustrates the lack of cytotoxicity of the degradable P(NIPAAm-co-NHS) copolymer. Cytotoxicity was assessed by culturing smooth muscle cells (SMC) on tissue culture plate (TCPS) supplemented with copolymer-containing medium. Different concentrations of copolymer were assessed. The cell viability was measured by MTT assay on day 1 and on day 3. As the final degradation product of P(NIPAAm-co-NHS) copolymer is P(NIPAAm-co-AAc) copolymer, P(NIPAAm-co-AAc) copolymer was used to assess cytotoxicity. There is no significant difference in cell viability between those plated on control medium or on medium supplemented with the copolymer.

Figure 32:
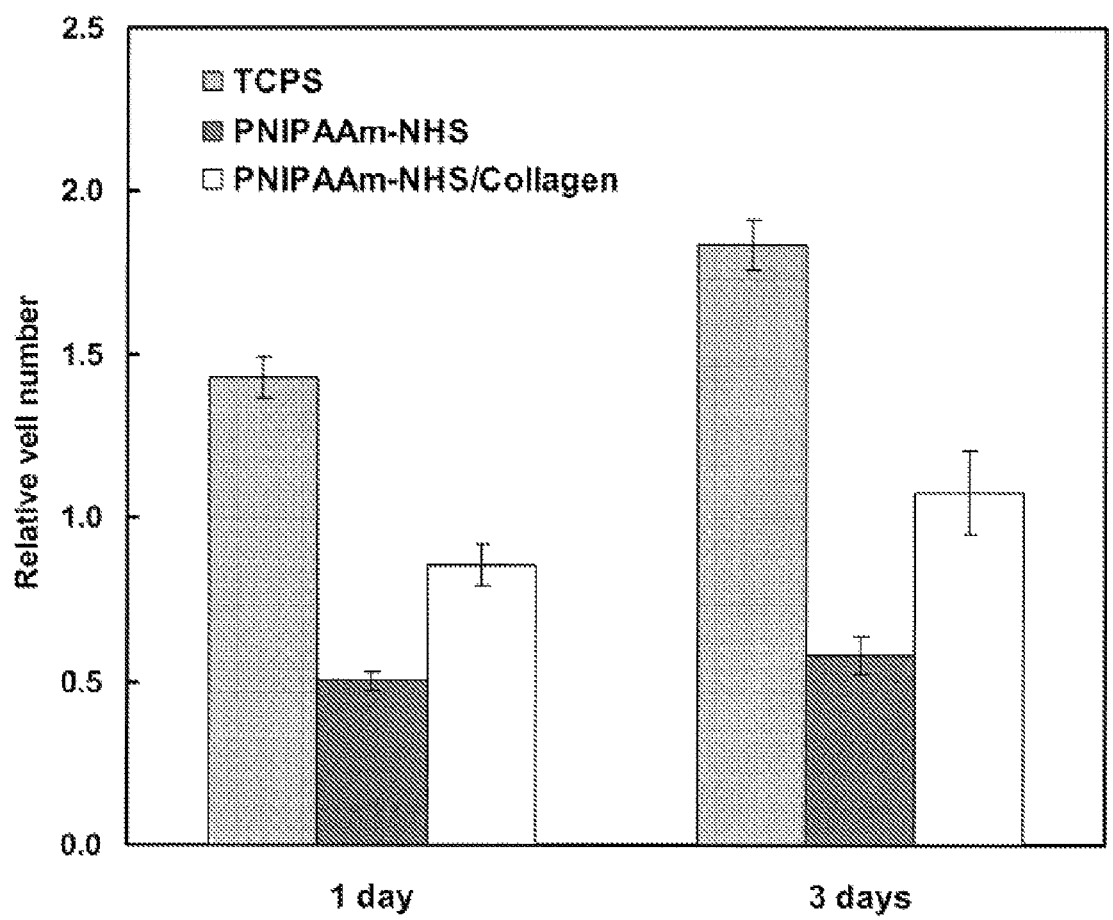
FIG. 32 is a graph showing the viability of SMC on the surface of the P(NIPAAm-co-NHS) copolymer, where cell adhesion relative to the tissue culture plate (% TCPS) increases with the conjugation of collagen to the copolymer.

FIG. 32 shows the viability of SMC on the surface of P(NIPAAm-co-NHS) copolymer. Cell adhesion relative to the tissue culture plate (% TCPS) is seen to increase with the conjugation of collagen to the copolymer. SMCs were cultured on the surface of the copolymer. Tissue culture plates (TCPS) were used as control. At day 1, the copolymer without collagen showed 35% of cell adhesion as compared with TCPS. The conjugation of collagen increases cell adhesion to 49%. Cells grew on the copolymer during the culture, as the relative cell number on day 3 is higher than on 1 day.

Figure 33:
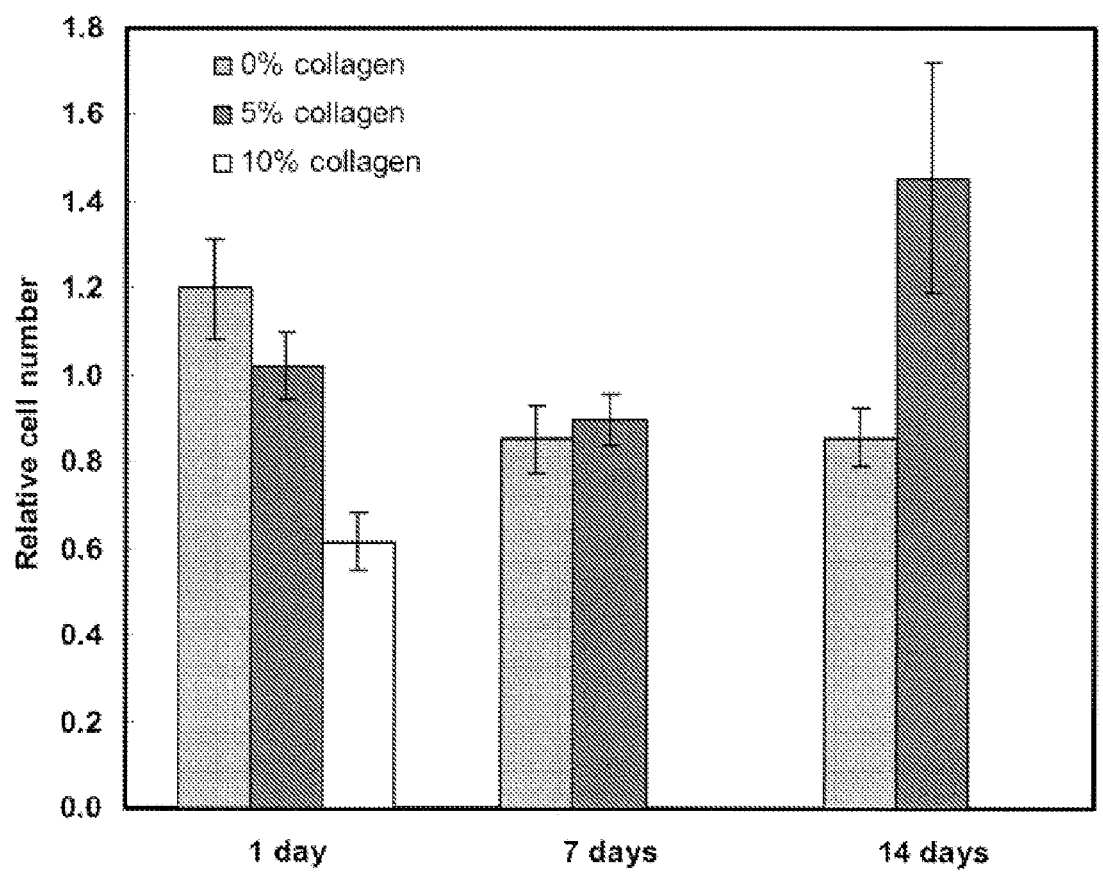
FIG. 33 is a graph showing the viability of SMC encapsulated within the P(NIPAAm-co-NHS) copolymer, where conjugation of collagen to the copolymer increases viability at 14 days.

FIG. 33 illustrates the viability of SMC encapsulated within the copolymer P(NIPAAm-co-NHS) 93.5/6.5. Conjugation of collagen to the copolymer increases viability at 14 days. Encapsulation of cells within copolymer was conducted by mixing $5 \times 10^6$/mL RSMCs with copolymer or copolymer/collagen aqueous solution. Cell adhesion and growth were quantified with the MTT mitochondrial assay. Cell viability was characterized by Live/Dead® staining. Copolymer with 5% collagen has slightly lower cell number as compare with copolymer without collagen. However, copolymer with 10% collagen has significantly lower cell number. Cell number decreased in copolymer without collagen during the culture. In contrast, cell number increased at 14 days for copolymer with collagen.

Figure 34A:
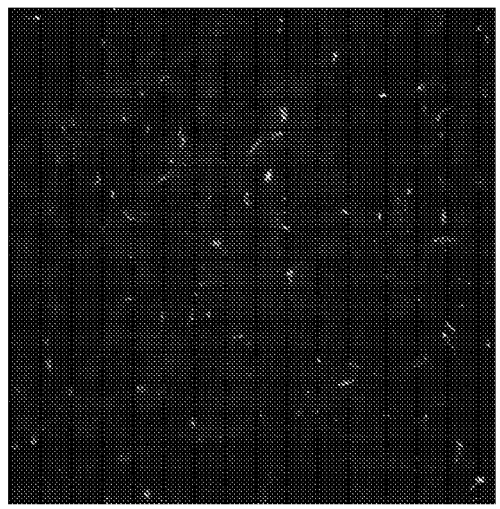
FIG. 34A is a microphotograph of SMC encapsulated within P(NIPAAm-co-NHS) copolymer, where the Live/Dead® (Invitrogen of Carlsbad, Calif.) staining stains the live cells green and the dead cells red.
Figure 34B:
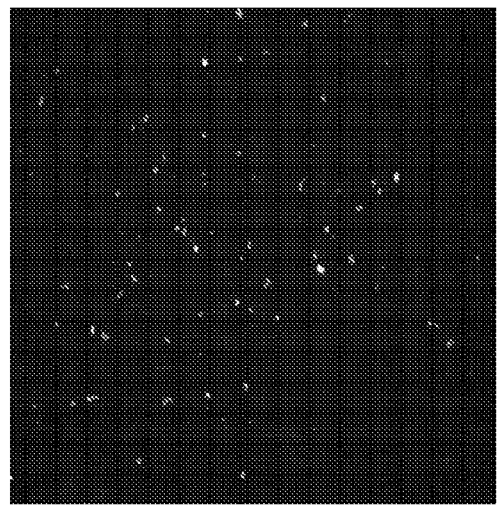
FIG. 34B is a microphotograph of SMC encapsulated within P(NIPAAm-co-NHS) copolymer conjugated with collagen, where the Live/Dead® staining stains the live cells green and the dead cells red.

FIG. 34A is a photomicrograph obtained after a Live/Dead® stain of SMC encapsulated within the P(NIPAAm-co-NHS) copolymer. FIG. 34B is a photomicrograph obtained after a Live/Dead® stain of SMC encapsulated within the P(NIPAAm-co-NHS) copolymer conjugated with collagen. Live cells are stained red and the dead cells are stained green.

Example 3

Flexible, Injectable and Thermosensitive Poly(NIPAAm-co-AAc-co-NHS-co-HEMAPTMC) Hydrogel The polymer comprised residues of: N-isopropylacrylamide (NIPAAm) as thermosensitive component after polymerization; acrylic N-hydroxysuccinimide ester (NHS) for conjugation of biomolecules; acrylic acid (AAc) for improvement of hydrophilicity; and poly(trimethylene carbonate) macromer for introduction of degradability and hydrophobicity. The biodegradable polymer backbone comprised of a poly(trimethylene carbonate) hydroxyethyl methacrylate-trimethylene carbonate (HEMAPTMC) macromer.

Poly(trimethylene carbonate) macromer HEMAPTMC was synthesized by ring-open polymerization of trimethylene carbonate (TMC) with 2-hydroxyethyl methacrylate using stannous octoate as catalyst. Reaction was conducted at 110° C. for 1 hour under a nitrogen atmosphere. Poly(trimethylene carbonate) macromers with various TMC units were synthesized by altering the feed ratio of TMC and HEMA. Feed ratios of HEMA/TMC were ½ and ⅓, and the corresponding TMC units in the macromers, as determined by NMR were 2.0 and 4.2, respectively. Copolymers were synthesized from NIPAAm, AAc, NHS, and HEMAPTC by free radical polymerization in 1,4-dioxane at 70° C.

Type 1 Collage (4 wt %) was conjugated with P(NIPAAm-co-AAc-co-NHS-co-HEMAPTMC) at 20 wt % in PBS (pH=7.4) at 4° C. for 24 h. Hydrogels were formed at 37° C. and cut into 6 mm×0.5 mm discs. Rat arterial smooth muscle cells (SMCs) were statically seeded at a density of $3 \times 10^5$/mL for cytocompatibility studies. For encapsulation studies, SMCs with $5 \times 10^6$/mL were mixed with copolymer solution or mixture of copolymer and collagen. The hydrogel was then cultured in medium of 20% fetal bovine serum in PBS. Cells in hydrogel were visualized after stained with live cell stain CMFDA. Many of the experimental procedures discussed in the previous Examples were used within this Example, unless otherwise specified.

Figures 35A, 35B:
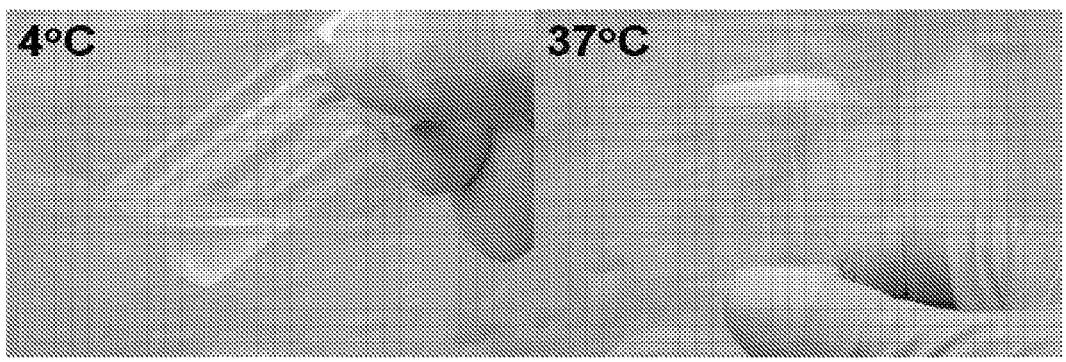
FIGS. 35A-35D are macroscopic photographs of the P(NIPAAm-co-AAc-co-NHS-co-HEMAPTMC) copolymer at different temperatures and stretching conditions.
Figures 35C, 35D:
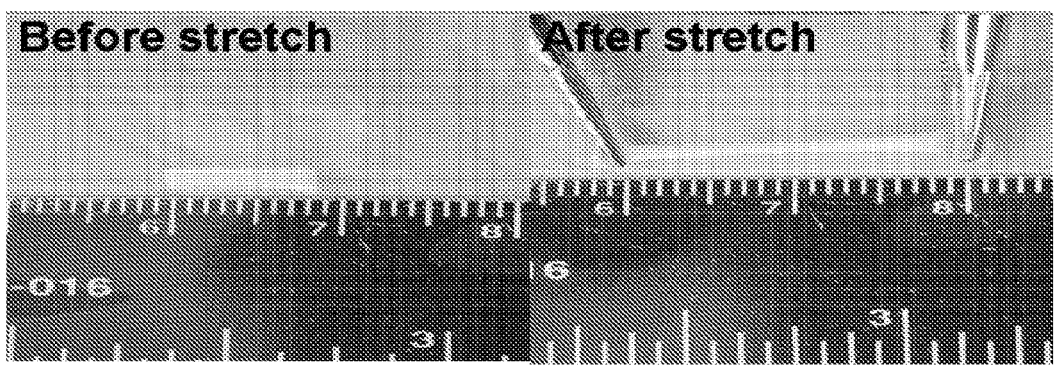

Macromers HEMAPTMC with different TMC lengths were characterized by $^1$H-NMR. Hydrogel structure and composition were confirmed and characterized by FTIR, $^1$H-NMR, and DSC. Copolymers were soluble and injectable in PBS at 4° C. (FIG. 35A) and formed hydrogels when gelled at 37° C. (FIG. 35B). The hydrogels had measured LCSTs between 16 to 20° C. before degradation. After complete hydrolysis with NaOH, the hydrogels had LCSTs above 39.7° C. and were soluble in PBS at 37° C. Incorporation of collagen with P(NIPAAm-co-AAc-co-NHS-co-HEMAPTMC) slightly increased LCSTs. At 37° C., water absorption was 47-85% without collagen and increased to over 102% when collagen was incorporated. Hydrogels were flexible and strong, with elongation breaks from 844 to 2625% and tensile strengths from 0.59 to 0.85 MPa at 37° C. FIG. 35C shows the hydrogel before stretching, where FIG. 35D shows the hydrogel after stretching to ~2 times its original length.

Figure 36A:
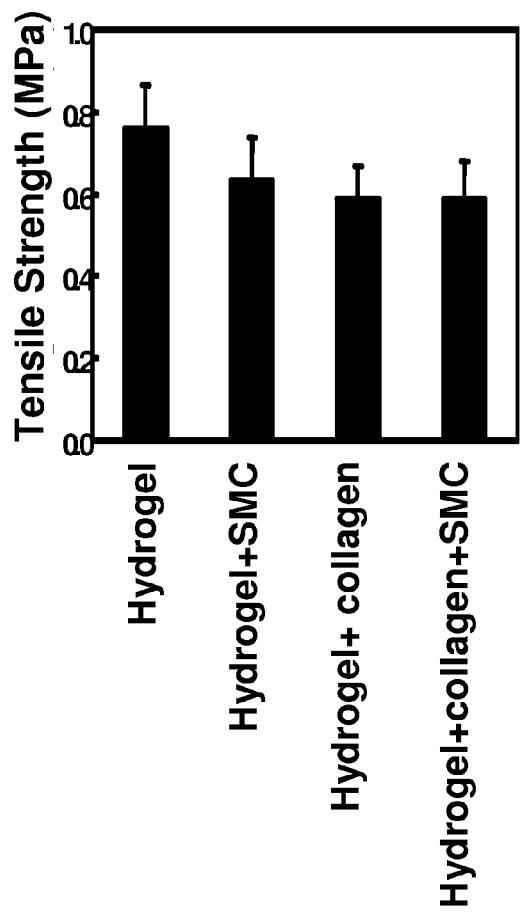
FIGS. 36A-36B are graphs showing the mechanical properties of the (NIPAAm-co-AAc-co-NHS-co-HEMAPTMC) copolymer, the copolymer with SMCs, the copolymer with collagen, and the copolymer with collagen and SMCs.
Figure 36B:
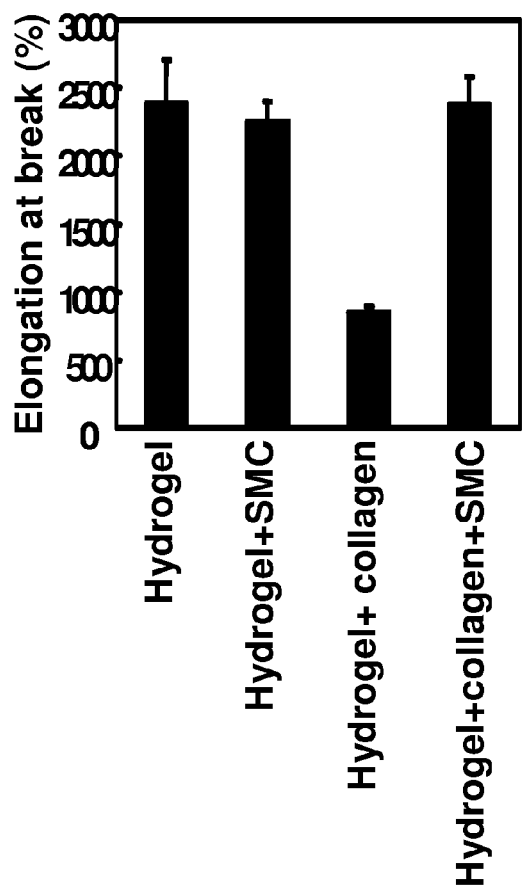

Hydrogels had weight loss from 16-84% over three weeks in PBS at 37° C., depending on the TMC length and the polymer composition. Polymers conjugated with collagen showed higher weight loss that the corresponding polymer. Degradation products were non-cytotoxic. Cell adhesion on hydrogels was 57% of that on TCPS (p<0.01) and increased with collagen conjugation. SMCs were successfully encapsulated in hydrogels and encapsulation efficiency was greater than 97%. SMC encapsulation did not significantly change the hydrogel's mechanical properties. FIG. 36 shows the tensile strength (MPa) and elongation at break (%) for the copolymer (NIPAAm-co-AAc-co-NHS-co-HEMAPTMC) with collagen, without collagen, with SMCs, and with collagen and SMCs. Cell number in collagen conjugated copolymer increased during 7 days in culture, while it increased during the first 3 days and decreased after 7 days in culture in pure copolymer.

Example 4

In Vivo Injection of Poly(NIPAAm-co-AAc-co-NHS-co-HEMAPLA Ester) Copolymer into a Porcine Model Biomaterial injection therapy may be a viable option for treatment of cardiac failure. Injection of a non-contractile material into the border zone and infarct region of the cardiac wall may benefit cardiac mechanics. An optimal injection material would possess beneficial mechanical properties in situ, biodegradability, and additional biofunctionality.

Figure 37A:
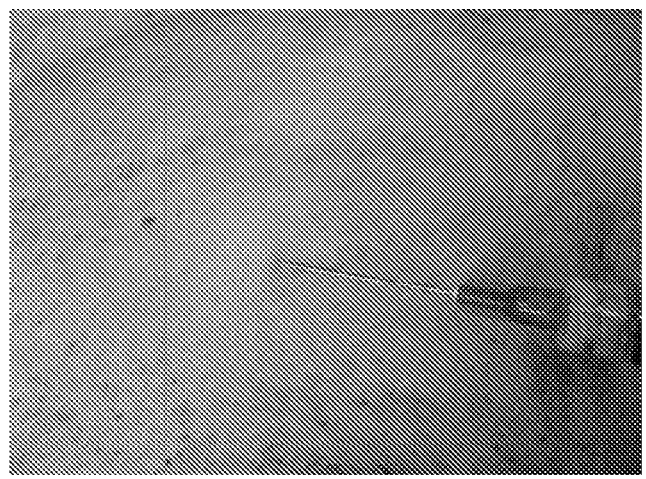
FIGS. 37A-37C are macroscopic photographs of a subcutaneous injection of one embodiment of the copolymers described herein, namely NIPAAm/AAc/NHS/HEMAPTMC, ratio 85/6/5/4 copolymer, into a porcine model.
Figure 37B:
Figure 37C:
Figure 38A:
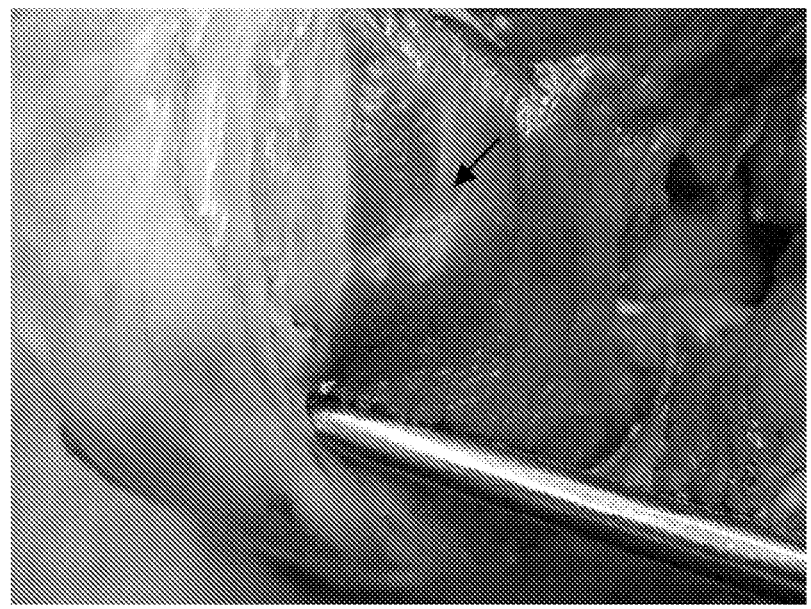
FIGS. 38A-38B are macroscopic photographs of a subcutaneous injection of NIPAAm/AAc/NHS/HEMAPTMC, ratio 85/6/5/4 copolymer into the myocardium of a porcine model.
Figure 38B:
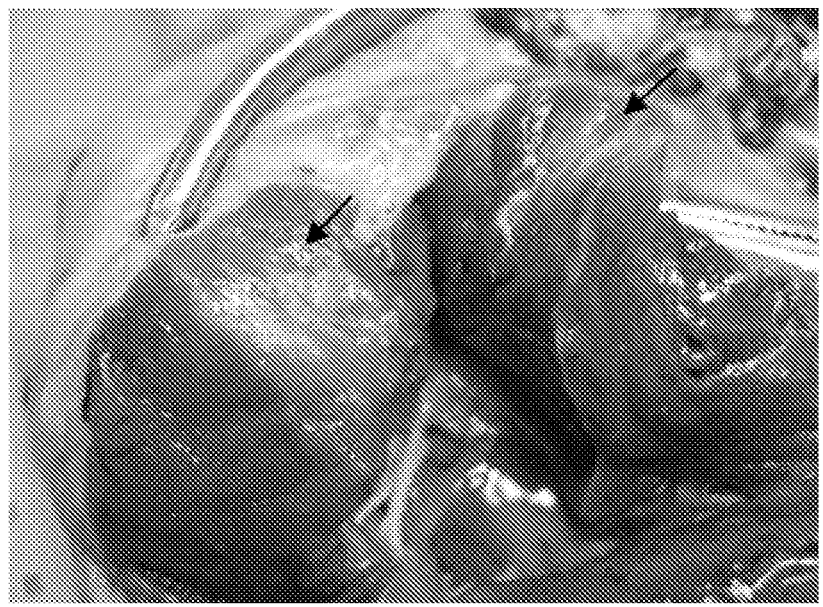

Solutions of NIPAAm/AAc/NHS/HEMAPTMC ratio 85/6/5/4. copolymer comprising a hydrogel containing 2.1 polylactide units, were injected into an in vivo porcine model. Injection sites included a sub-cutaneous/sub-fascia injection in a porcine model and an injection into the myocardium of the heart in a porcine model and FIG. 37 shows photographs of the sub-cutaneous/sub-fascia injection, where FIG. 38 shows photographs of the myocardial injection. These initial trials demonstrate the feasibility of intramuscular injection of the polymer solution.

Trials were conducted to determine the feasibility of polymer injection into a heart model from healthy pigs (N=2, BW=63 kg and 70 kg). Before injection, polymer solutions were stored on ice. Injection of the polymer was conducted with various gauges of needles with 3 mL syringes. Table 5 shows the effect of needle gauge on the pressure required to inject the solution out of the needles and the back flow from the puncture site. Though back flow is a concern, this can be addressed with needle selection and injection technique.

TABLE 5

Needle selection to optimize for polymer injection

| Needle gauge | Resistance during injection | Back flow from puncture site |
| --- | --- | --- |
| 26G | Impossible to inject | |
| 23G | Possible to inject with little resistance | |

TABLE 5-continued

Needle selection to optimize for polymer injection

| Needle gauge | Resistance during injection | Back flow from puncture site |
| --- | --- | --- |
| 20G | Possible to inject with little resistance | + |
| 18G | Possible to inject | ++ |
| 16G | Possible to inject | +++ |

The present invention has been described with reference to certain exemplary embodiments, dispersible compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiments, but rather by the appended claims as originally filed.

We claim:

1. A copolymer comprising: an N-isopropylacrylamide residue; an acrylic acid residue; an acrylic acid N-hydroxysuccinimide ester residue; and a polyester macromer comprising hydroxyethyl methacrylate (HEMA) and trimethylene carbonate (TMC), wherein hydrogels comprising said copolymer have weight loss ranging from 16% to 84% over three weeks in phosphate-buffered saline at 37° C.; and
wherein the percent feed ratio of N-isopropylacrylamide: acrylic acid:acrylic acid N-hydroxysuccinimide ester: polyester macromer for the copolymer is 85: 6: 5: 4.

2. The copolymer of claim 1, wherein the copolymer has a lower critical solution temperature below 37° C.

3. The copolymer of claim 1, wherein the copolymer has a lower critical solution temperature of between 30° C. and 35° C.

4. The copolymer of claim 1, wherein the copolymer has a lower critical solution temperature above 37° C. after its ester bonds are hydrolyzed.

5. The copolymer of claim 1, wherein the ratio of hydroxyethyl methacrylate to trimethyl carbonate residues in the polyester macromer ranges from 1:1 to 1:10.

6. The copolymer of claim 5, wherein the ratio of hydroxyethyl methacrylate and trimethyl carbonate residues in the polyester macromer ranges from 1:2 to 1:5.

7. The copolymer or claim 1, further comprising one or both of a caprolactone and a glycolide residue.

8. The copolymer of claim 1, further comprising an amine-containing compound attached to the copolymer.

9. The copolymer of claim 8, wherein the amine-containing compound is collagen.

10. The copolymer of claim 8, wherein the amine-containing compound is gelatin.

11. The copolymer of claim 9, comprising between 1% wt and 10% wt collagen.

12. A composition comprising the copolymer of claim 1, and an aqueous solvent.

13. The composition of claim 12, wherein the aqueous solvent is one of water, saline and phosphate-buffered saline.

14. The composition of claim 12, further comprising an active agent.

15. The composition of claim 14, wherein the active agent is one or more of an antiseptic, an antibiotic, an analgesic, an anesthetic, a chemotherapeutic agent, a clotting agent, an anti-inflammatory agent, a metabolite, a cytokine, a chemoattractant, a hormone, a steroid, a protein and a nucleic acid.

16. The composition of claim 15, wherein the active agent is a desmopressin.

17. The composition of claim 12, further comprising a biological material selected from the group consisting of a cell, a protein, and a virus.

18. The composition of claim 17, wherein the biological material is a cell.

19. The composition of claim 18, wherein the cell is a progenitor cell or a stem cell.

20. A method of making a thermosensitive copolymer comprising co-polymerizing N-isopropylacrylamide; acrylic acid; acrylic acid N-hydroxysuccinimide ester; and a polyester macromer prepared from hydroxyethyl methacrylate and trimethyl carbonate monomers to make a copolymer,
wherein the percent feed ratio of N-isopropylacrylamide: acrylic acid:acrylic acid N-hydroxysuccinimide ester: polyester macromer for the copolymer is 85:6:5:4; and
wherein hydrogels comprising said copolymer have weight loss ranging from 16% to 84% over three weeks in phosphate buffered saline at 37° C.

21. The method of claim 20, wherein the monomers are co-polymerized by free-radical polymerization.

22. The method of claim 20, wherein the ratio of hydroxyethyl methacrylate to trimethyl carbonate residues in the polyester macromer ranges from 1:1 to 1:10.

23. The method of claim 20, wherein the ratio of hydroxyethyl methacrylate to trimethyl carbonate residues in the polyester macromer ranges from 1:2 to 1:5.

24. The method of claim 20, further comprising conjugating an amine-containing compound to the copolymer.

25. The method of claim 24, wherein the amine-containing compound is collagen.

26. The method of claim 24, wherein the amine-containing compound is gelatin.

27. The copolymer of claim 1, having a tensile strength of 0.5 MPa to 1.14 MPa.

28. The copolymer of claim 8, having a tensile strength greater than 0.3 MPa and an elongation at break greater than 340%.

* * * * *